United States Patent [19]
Hale et al.

[11] Patent Number: 4,925,804
[45] Date of Patent: May 15, 1990

[54] INTERLIGAND METAL TRANSFER ASSAY

[75] Inventors: Ron L. Hale, Woodside; Irwin Wieder, Los Altos, both of Calif.

[73] Assignee: Baxter International Inc., Deerfield, Ill.

[21] Appl. No.: 875,449

[22] Filed: Jun. 17, 1986

[51] Int. Cl.$^5$ .................. G01N 33/566; G01N 21/76
[52] U.S. Cl. ................... 436/501; 436/500; 436/504; 436/517; 436/536; 436/537; 436/172; 436/805; 436/518; 435/6
[58] Field of Search .................. 435/6; 436/500, 501, 436/504, 517, 537, 82, 172, 518, 525, 800, 805, 808; 530/304

[56] References Cited

U.S. PATENT DOCUMENTS

| | | | |
|---|---|---|---|
| 3,901,654 | 8/1975 | Gross | 23/230 B |
| 3,939,350 | 2/1976 | Kronick et al. | 250/365 |
| 4,020,151 | 4/1977 | Bolz et al. | 424/1.5 |
| 4,058,732 | 11/1977 | Wieder | 250/461 |
| 4,150,295 | 4/1979 | Wieder | 250/458 |
| 4,220,450 | 9/1980 | Maggio | 23/230 B |
| 4,283,382 | 8/1981 | Frank et al. | 424/8 |
| 4,341,957 | 6/1982 | Wieder | 250/461.2 |
| 4,352,751 | 10/1982 | Wieder et al. | 260/112 R |
| 4,374,120 | 2/1988 | Soini et al. | 436/546 |
| 4,565,790 | 1/1985 | Hemmila et al. | 436/537 |

FOREIGN PATENT DOCUMENTS

| | | |
|---|---|---|
| 0064484 | 4/1982 | European Pat. Off. |
| 0159066 | 4/1982 | European Pat. Off. |
| 0068875 | 6/1982 | European Pat. Off. |
| 0103558 | 9/1983 | European Pat. Off. |
| 0154788 | 1/1986 | European Pat. Off. |
| 3239410 | 10/1982 | Fed. Rep. of Germany |
| 57-149965 | 3/1981 | Japan |

OTHER PUBLICATIONS

Wieder, I., 1978 Elsevier/North Holland Biomedical Press Immunofluorescence and Related Staining Techniques W. Knapp, K. Holubar and G. Wick eds.
Hemmila, I., et al., Analytical Biochemistry 137 335 (1984)—Europium as a Label in Time Resolved Immunofluorometric Assays.
Soini, E., et al., Clin. Chem. 29/1, 65-68 (1983) Time Resolved Fluorometer for Lathanide Chelates—A New Generation of Nonisotopic Immunoassays.
Malmivuo, J., et al., Proceedings of the Fourth National Meeting on Biophysics and Medical Engineering and the Third National Meeting in Industry Tampere Finland.
Ann Clin. Biochem. 1981 18 253-274 A review of fluoroimmunoassay and immunofluorometric assay D. S. Smith M. Al-Hakiem and J. Landon.

Primary Examiner—Robert J. Warden
Assistant Examiner—Toni R. Scheiner
Attorney, Agent, or Firm—Irell & Manella

[57] ABSTRACT

A new reporter mechanism for biospecific reactions is disclosed. This mechanism involves interligand metal ion transfer in which a metal ion is directly transferred from one chelate complex to another following the occurance of the biospecific reaction. The second chelate complex is separate from and detectably different than the first chelate complex. This invention can take the form of methods of chemical analysis and kits for conducting such methods. In preferred embodiments of this invention the detectable difference is a difference in fluorescence, such as an increase or decrease which occurs as a result of the formation of the second chelate. In further preferred embodiments the difference in fluorescence is detected using fluorescent background rejection methods.

17 Claims, 2 Drawing Sheets

INTERLIGAND METAL TRANSFER ASSAY

CROSS-REFERENCES TO RELATED APPLICATIONS

Several of the ligands which can be employed in the present invention are disclosed and claimed in copending U.S. patent application Ser. No.712,774 of Hale and Solas filed Mar. 18, 1985 now U.S. Pat. No. 4,761,481; the techniques of this invention find application in the homogeneous assay methods disclosed and claimed in copending U.S. patent application Ser. No. 875,287 filed of even date herewith; which are incorporated herein in their entirety by reference.

BACKGROUND OF THE INVENTION

1. Field of the Invention

This invention relates to a reporter mechanism useful in analytical chemistry. More particularly, it relates to a reporter mechanism for use in conjunction with specific binding assay techniques to achieve highly sensitive determinations of analytes in test samples.

Specific binding assay techniques are useful for determining various substances of diagnostic, medical, environmental and industrial importance which appear at very low concentrations. Specific binding assays are based on a specific interaction between the analyte under determination and a binding partner therefor. Where one of the analyte and its binding partner is an antibody and the other is a corresponding hapten or antigen, the assay is known as an immunoassay.

In such assays, it is necessary to have a reporter mechanism or event, for example, measurement of a label, which can give a measurable indication of the extent to which the specific binding reaction takes place. For example, radioactive or fluorescent labels can be present on the binding partner and the presence of this radioactive or fluorescent label in the specifically bound pair can be used to detect formation of the pair. Alternatively, the specific binding reaction can give rise to a change in the detectable properties of the reporter group, for example by increasing or decreasing a measurable property.

Reporter mechanisms and labels are employed in heterogeneous analysis settings and homogeneous assay settings. A heterogeneous assay is one in which the labeled specifically bound pair is physically separated from unbound labels. A homogeneous assay is one in which the labeled pairs are not separated from the unbound labels but the bound labels and unbound labels are distinguishable from one another. See J. BIOL. CHEM., 251, 4172–8 (1976).

2. Description of Prior Art

The present reporter mechanism involves interligand transfer of metals. Metals have been used in reporter mechanisms heretofore. In one elementary art-taught method, a species containing a metal ion is determined by measuring the amount of the metal in the sample by conventional wet chemistry quantitative or qualitative analysis methods.

In another method of the art a nonmetal-containing species is determined by reacting it with a metal-containing material in a biospecific reaction to form a metal-containing specific binding pair and thereafter determining the amount of metal associated with the pair and thus indirectly the amount of the nonmetal species. One embodiment of such a process is shown in U.S. Pat. No. 4,341,957, issued Jul. 27, 1982 in which analysis methods involving an antibody labeled with a fluorescent rare earth metal chelate reacting with its corresponding antigen are shown. Thereafter the amount of fluorescent chelate associated with the pair is determined fluorometrically. Some references generally to tagging of biospecific molecules with metal ions include, for example, U.S. Pat. Nos. 4,283,382; 4,352,751; 4,374,120; and 4,565,790, Europoean patent application Nos. 0154788, 0159066, and 064484 as well as Japanese Pat. No. 57,149,965 and German patent application No. 3239410-Al.

U.S. Pat. Nos. 4,058,732 and 4,150,295, issued on Nov. 15, 1977 and Apr. 17, 1979, respectively and a chapter appearing at pages 67–80 of *Immunofluorescence and Related Staining Techniques*, Knapp, et al., eds. (1978, Elsevier/North Holland Biomedical Press) describe the use of fluorescent background rejection in assay techniques and disclose that rare earth metal chelates are attractive fluorescent species. This art-taught background rejection relies on time gating and measures longlived fluorescence from the assayed species after shortlived background fluorescence has decayed. This background rejection technique is employed in certain embodiments of this invention.

U.S. Pat. No. 4,352,751 issued on Oct. 5, 1979 discloses a family of rare earth metal chelates and their use in fluorescent background rejection techniques. Similarly, European patent application No. 68875 A2 filed on Jun. 28, 1982 of Eastman Kodak Co. discloses fluorescent rare earth chelate labels in fluoroassay techniques.

ANALYTICAL BIOCHEMISTRY, 137, 335 (1984) and European patent application No. 64484 A2 of Wallac Oy disclose a heterogeneous assay method named the "dissociation-enhanced lanthanide fluoroimmunoassay" or "DELFIA". These assays are either solid phase sandwich assays or solid phase competitive assays. In the first case, solid phase first antibody binds a two-site antigen which then binds a europium chelate-labeled second antibody. In the second case, solid phase antigen competes with free antigen for a limited amount of free europium chelate-labeled antibody. In either case, following a separation step, the europium-labeled antibody ends up on the solid phase. The materials used in these methods give a relatively low fluorescence chelate which is not detectable at desired levels of sensitivity. Thereafter the solid phase chelate is treated with an acidic (pH about 3.2) enhancement solution which causes the metal to be released from the solid chelate into solution. The enhancement solution also contains a $\beta$-diketone which chelates the freed ions leading to development of fluorescence. Because of insolubility of the $\beta$-diketone in aqueous solutions, the enhancement solution also must contain a detergent (Triton X-100) to solubilize both the $\beta$-diketone and an added synergistic agent (tri-N-octylphosphine oxide, TOPO,) which is also water immiscible. These materials are employed to yield a micellar system and rely upon the release of the metal ion from the first complex and its later chelation by the $\beta$-diketone to provide the detectable fluorescent species. The lanthanide ion label that is released from the chelate by an acid treatment can be measured using the fluorescence background rejection technique.

Other references of interest include articles appearing at CLIN. CHEM., Winston Salem, N.C., 29(1) 65–8 (1983) and PROC. NATL. MEET. BIOPHYS. MED. ENG, FINL., 4, 199–202 (1982), European patent application No. 103558 published Mar. 21, 1984, and U.S. Pat. No. 4,374,120 all from the Wallac Oy group; and Kodak's U.S. Pat. No. 4,283,382, issued Aug. 11, 1981.

Other art to be noted includes the article "A Review of Fluoroimmunoassay and Immunofluorometric Assay", D. S. Smith et al, ANN. CLIN. BIOCHEM., 18, (1981) 253–274 which provides a summary of the heterogeneous and homogeneous fluoroassay techniques proposed heretofore; U.S. Pat. Nos. 3,998,943; 4,020,151; 3,939,350; 4,220,450 and 3,901,654 which show analytical assay techniques. A number of additional references to various general homogeneous assay techniques are provided in the patent application filed of even date herewith and incorporated herein by reference.

BRIEF DESCRIPTION OF THE INVENTION

A new reporter mechanism for biospecific reactions has now been found. This mechanism involves interligand metal ion transfer following a biospecific reaction. In this mechanism a metal ion is directly transferred from a first chelate complex with a first ligand to a second ligand thereby forming a second chelate complex which is separate from and detectably different than the first chelate complex. This reporter mechanism can find application in heterogeneous and homogeneous assays employing competitive or direct (immunometric) measurement schemes.

This invention can be embodied as analysis methods for determining the presence or amount of an analyte in test materials. In the case of a heterogeneous competitive assay (I), such a method can include the steps of a. biospecifically reacting in the presence of the test material two biospecific species, the first of which carries a first metal ion chelate and competes with the analyte, if present, for a reaction-limiting amount of one or more biospecific binding sites on the second species thereby forming a biospecific reaction product, b. separating the biospecific reaction product from unreacted first species and analyte, c. contacting the separated biospecific reaction product with an excess of a ligand which directly removes metal ion from the first metal ion chelate and forms a second metal ion chelate which is separate from and detectably different than the first metal ion chelate, d. detecting the presence of the second metal ion chelate and e. relating the detected presence of the second metal ion chelate to the presence of the analyte in the test sample.

In a variation of this assay (I), in step a. a reaction-limiting amount of a first metal ion chelate can be used in conjunction with a second species which competes with the analyte in place of the reagents described above.

A heterogeneous direct assay (II) employing the present reporter mechanism can include the steps of a. contacting the test material with an excess of a biospecific partner for the analyte, thereby biospecfically coupling any analyte present in the test sample to form a first biospecific pair, b. contacting the first biospecific pair with an excess of a second biospecific partner for the analyte which partner carries a first metal ion chelate thereby forming a first metal ion chelate-labeled biospecific trio;

c. separating the biospecific trio from unreacted second biospecific partner, d. contacting the separated biospecific trio with an excess of a ligand which directly removes metal ion from the first metal ion chelate and forms a second metal ion chelate which is separate from and detectably different than the first metal ion chelate and the metal ion-containing biospecific trio, e. detecting the presence of the second metal ion chelate and f. relating the detected presence of the second metal ion chelate to the presence of the analyte in the test sample.

In the case of a homogeneous competitive assay (III), such a method can include the steps of a. biospecifically reacting in the presence of the test material two biospecific species, one of which carries a first metal ion chelate and the other of which carries a second metal ion chelate-forming ligand. The second of these two species competes with the analyte, if present, for a reaction-limiting amount of one or more biospecific binding sites on the first species thereby forming a biospecific reaction product that can include the couple of the first and second species and the couple of the first species and the analyte. The ligand on the second species is positioned in such proximity to its biospecific group that as a result of the biospecific reaction the ligand can contact and react with the first metal ion chelate carried by the first species, b. incubating the product of the biospecific reaction for a period sufficient to effect direct interligand transfer of metal ion from the first metal ion chelate to the second metal ion chelate-forming ligand thereby forming a second metal ion chelate complex, c. detecting the presence of the second metal ion chelate and d. relating the detected presence of the second metal ion chelate to the presence of the analyte in the test sample.

In a variation of this method (III) the analyte can compete with the metal ion chelate carrying species for a limiting amount of the species carrying the second chelate-forming ligand.

In the case of a homogeneous immunometric assay (IV), such a method can include the steps of a. biospecifically reacting in the presence of the test material two biospecific species, one of which carries a first metal ion chelate and the other of which carries a second metal ion chelate-forming ligand. Each of these species are present in excess and biospecifically react with the analyte if present but with different sites thereon. The chelate on the first species and the ligand on the second species are each positioned in such proximity that as a result of the biospecific reactions the ligand can contact and react with the first metal ion chelate, b. incubating the product of the biospecific reacting for a period sufficient to effect direct interligand transfer of metal ion from the first metal ion chelate to the second metal ion chelate-forming ligand thereby forming a second metal ion chelate complex, c. detecting the presence of the second metal ion chelate and d. relating the detected presence of the second metal ion chelate to the presence of the analyte in the test sample.

In preferred embodiments of this invention the detection of the second metal ion chelate is carried out by detecting a difference in fluorescence, such as an increase or decrease in fluorescence which occurs when the second chelate is formed. In further preferred embodiments the difference in fluorescence is detected using fluorescent background rejection methods.

In other aspects, this invention provides assay kits including the reagents necessary to conduct the above-described methods.

DETAILED DESCRIPTION OF THE INVENTION

Brief Description of the Drawings

In this specification reference will be made to the accompanying drawings in which.

Description of Preferred Embodiments

Figure 1:
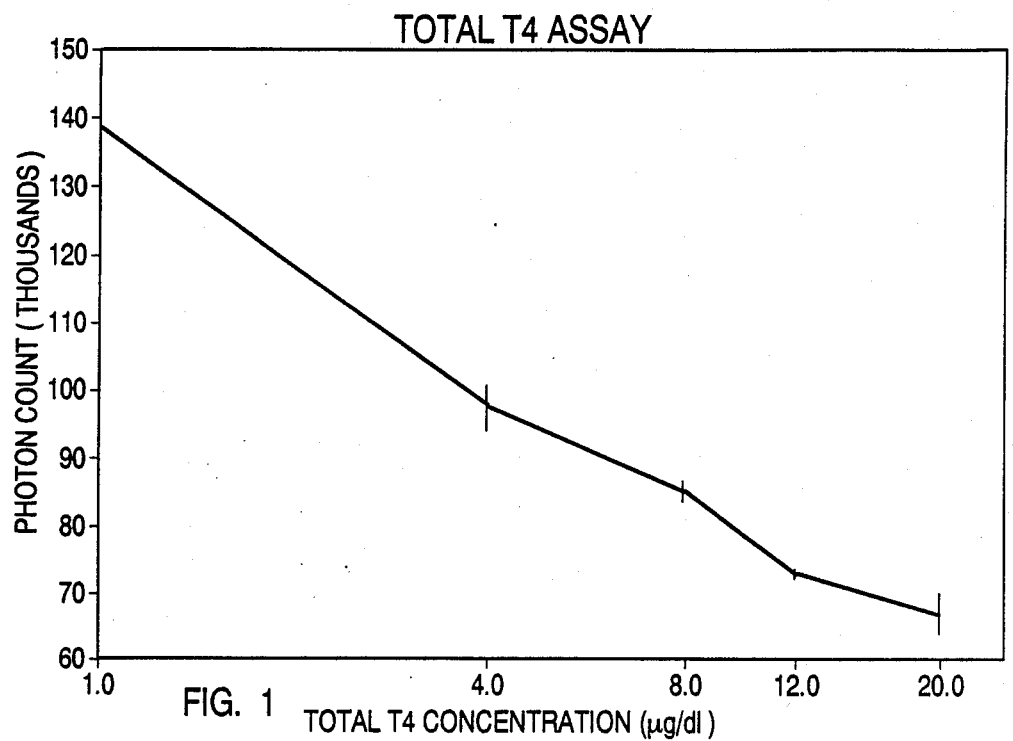
FIGS. 1 through 4 are graphs illustrating analysis results obtained with the reporter mechanism of the invention.

In accord with the present invention assays are carried out using metal transfer as the reporter mechanism. This mechanism calls for a metal ion to be transferred between two chelating ligands. That is, the metal ion is not released into solution and then chelated but rather it directly transfers from the first chelate to the second. These two chelate complexes are separate from one another and they are distinguishable from one another so that the appearance of the second complex can be detected. When the appearance of the second complex can be related to the occurence of a biospecific reaction, this mechanism serves as a reporter for the occurance of the reaction. As used in this application, the terms "ligand" and "chelate" have their conventional meanings—a ligand is a group which can form a complex with a metal—a chelate is a complex which includes a metal ion and at least one polydentate ligand.

In the following detailed description, this mechanism and these groups are described in order as:
The Metal Ions
The Chelating Ligands
The Biospecific Groups
The Links to the Biospecific Groups and
The Analyte Species
Reporter Mechanism and Analysis Methodologies

The Metal Ions

In the reporter of the present invention, a metal ion is directly transferred between two chelate complexes. The metal ion which is transferred can be any metal that is capable of forming two chelate complexes that present measurably different properties. As a general rule, such metal ions are usually polyvalent metal ions, in particular the rare earth and transition metal ions. For example, the metal ions may be selected from transition metal ions such as $Al^{+++}$, $Cd^{+++}$, $Co^{++}$, $Co^{+++}$, $Cr^{++}$, $Cr^{+++}$, $Cu^{++}$, $Fe^{++}$, $Fe^{+++}$, $Mn^{++}$, $Mn^{+++}$, $Ni^{++}$, $Sb^{+++}$, $Sn^{++}$, $V^{+++}$, $V^{++++}$, $Zn^{++}$, and $Zr^{++++}$ which can form complexes having differing physical properties, for example spectral properties, with various chelating ligands. Another group of representative and preferred metal ions are the rare earth metal ions of both the actinide series and the lanthanide series which are capable of forming fluorescent chelate complexes. Representative examples of these ions include $Nd^{+++}$, $Pm^{+++}$, $Sm^{+++}$, $Eu^{+++}$, $Gd^{+++}$, $Tb^{+++}$, $Dy^{+++}$, $Er^{+++}$ and the like. The ions of the lanthanides are preferred rare earth metal ions with terbium ($Tb^{+++}$) and europium ($Eu^{+++}$) being the most preferred rare earth metal ions. As used herein, the term "fluorescent" is defined broadly to include phosphorescence and other forms of luminescence.

The Chelating Ligands

Two chelating ligands are employed in the reporter mechanism of this invention. One is attached to the metal initially. The other complexes the metal to form the second chelate. Both of the ligands should have the property of forming stable complexes. It is important to stress the stability property of the two chelates in this setting. Both of the chelates must be strong enough to hold the metal at high dilutions and in the presence of other species in the test samples such as serum components and the like which could compete for the metal ions.

The two ligands should be such as to give a change in a measurable property when the metal ion has been transferred from one to the other. This property could be, for example, fluorescence, with the change being in intensity, in wavelength, in polarity, or in lifetime, for example; infrared, visual or ultraviolet absorption spectrum; nuclear magnetic resonance, and the like. The precise nature of the changed property will depend upon the metal and the ligands employed, but in general, the rare earth chelates will generally be involved in fluorescence and spectral changes while the transition metal chelates will generally be involved in spectral changes, with a change from di- or tridentate ligands to penta- or hexadentate ligands in the transition metal complexes leading to such spectral changes.

The change in observed property can be an increase in property or it can be a decrease in the property. That is, the formation of the second chelate could cause a measurable increase in observed fluorescence, a measurable increase in spectral absorption at a particular wavelength, an increase in the wavelength of maximum absorption or emission, an increase in fluorescence lifetime, or the like or conversely, could cause a measurable decrease in such properties.

It usually is desirable for the initial metal chelate complex and the second-chelate-forming ligand and the resulting second chelate complex each to be water soluble since most of the media to be analyzed using the reporter mechanism are water based and it is often desired that the chelates and ligands be capable of being solubilized in these media.

The ligands employed in the present invention are characterized as being organic polydentate complex-forming materials. The functionalities in the ligands which can form the complexing bonds are hetroatoms or hetroatom-containing groups. Most commonly, these are aliphatic and aryl nitrogens and oxygens, although sulfur can be used as well. Representative complex bond-forming species include amine and amide groups—both alkyl and aryl, carbonyls, carboxyls, thiols, phosphates, and the like. Preferred ligands are organic groups containing from about 2 to about 40 carbon atoms and including from about 3 to about 10 such complex-forming species within a chain length of about 25 atoms. As will be set forth below, in some embodiments of this invention, one and sometimes both of the two ligands employed are attached to biospecific groups. These attachments are carried out through covalent bonds or equivalent links at positions on the ligands which do not adversely affect the properties of the ligand.

Examples of ligands useful for chelating with the metal ions in the present reporter mechanism include pyridine diacids of the formula

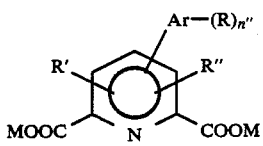

wherein Ar is an aryl, n'' is an integer equal to the number of available bonding sites on Ar, M is hydrogen or metal ion, and the n'' Rs, R' and R'' are each independently selected from hydrogen; electron-releasing groups including lower alkoxy, lower alkyl, amino, dialkylamino, aryl and aryloxy; and a linking group including a covalent bond and a bridge group capable of providing a link to a biospecific group subject to the provisos that at least one of the n'' Rs is an electron-releasing group and that at least one of R', R'' and the n'' Rs may, if called for, be a linking group to any biospecific remainder of the molecule. (As used throughout this application in reference to chemical group size, the term "lower" means eight carbon or less and preferably one to four carbon inclusive.) One of these substituents can supply the link to a biospecific group or the ligands may be used without an attached biospecific group if appropriate in the analysis scheme. These ligands can give rise to intensely fluorescent rare earth chelates. They have excitation maxima at wavelengths above 250 nm and as high as 350 nm. Thus, they are effective as second or receiving ligands in the transfer mechanism of this invention where an increase in fluorescence is desired. They also can form complexes with other metals. These ligands present unusual properties. Even though they are merely tridentate in structure, they are able to pull metals away from penta- and hexadentate ligands. This is unexpected because, as a general rule, a chelate's stability, i.e. difficulty of dissociation, is directly related to the number of sites in the ligand participating in the formation of the chelate. Other advantages of these materials are their ability to form solutions in a wide range of buffers and their ability to give intense fluorescence over a wide pH range of about 5–8.5.

Another family of suitable ligands are the 2,6-bis[N,N-di(carboxyalkyl)-aminoalkyl]pyridines—more particularly, a substituted aryl-substituted 2,6-[N,N-bis(-carboxylalkyl)-aminoalkyl]pyridine moiety which has the formula

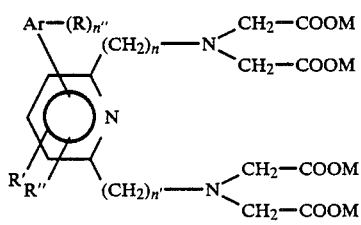

wherein n and n' are independently the integers 1 or 2, Ar is an aryl, n'' is an integer equal to the number of available bonding sites on Ar, M is hydrogen or metal ion, and the n'' Rs, R' and R'' are each independently selected as described hereinabove. These materials are described in the above-incorporated application of Hale and Solas. These materials also give rise to rare earth chelates having intense fluorescence emissions and thus could function as receiving or second ligands in systems where an increase in fluorescence is being detected. They also are potentially hexadentate or heptadentate materials so would lead to other metal chelates with appropriate properties. In fluorescence assays where a decrease in intensity is noted, they could function in the first chelates.

Other ligands which can form fluorescent chelates include polyamine-polycarboxylic acids such as the diamine triacids of the formula

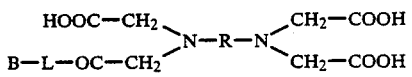

wherein B is a biospecific organic group if needed, L is the link to that biospecific group and R is a two carbon or larger covalent organic bridge. These materials are disclosed in U.S. Pat. No. 4,352,751 of Wieder and Wollenberg which is incorporated herein by reference. In general terms, these materials do not provide rare earth chelates which are as intensely fluorescent as obtained with the materials previously recited and thus could function as components of first chelates in systems where an increase in fluorescence is the detected change. Likewise, they are hexadentate ligands for transition metals and could function in combination with di- or tridentate materials with a spectral change as the detected event.

Other ligands include the triamine tetraacids of the formulae

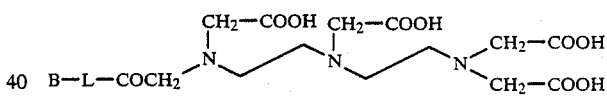

and

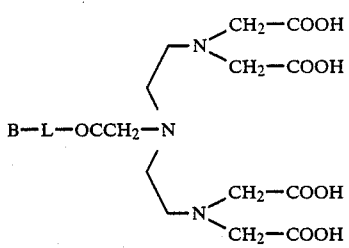

formed by the reaction of diethylenetriaminepentacetic acid in its dianhydride (Hnatowich, et al., INT. J. APPL. RADIAT. ISOT., 33, 327 (1982), activated mixed anhydride (Krejcarek and Tucker, BIOCHEM. BIOPHYS. RES. COMMUN., 77, 581 (1977), or active ester forms (Najafi, et al., INT. J. RADIAT. ISOT., 35, 554 (1984) with B and L being the optional biospecific groups (B) containing suitably substituted linker groups (L). These materials would take part in relatively less fluorescent chelates with rare earth metal ions as compared to the aryl amine materials shown above.

Still other suitable ligands include tetraacids of the formula

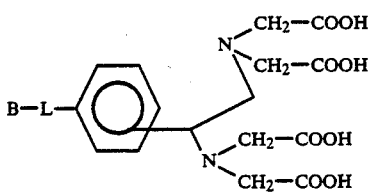

prepared from para-substituted phenyl ethylenediaminetetraacetic acids (Meares and Wensel, ACCOUNTS OF CHEMICAL RESEARCH, 17, 202 (1984)) and imidate-linked tetraacids of the formula

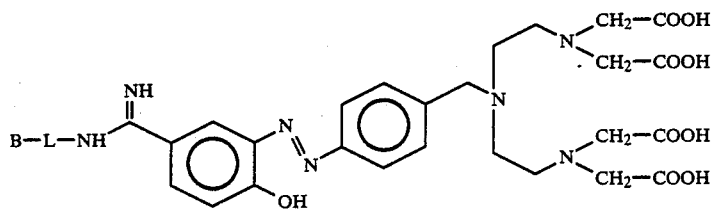

prepared from DTTA azo imidate (Paik, et al., J. RADIOANALYTICAL CHEMISTRY 57, 553 (1980)). As before B and L are the optional biospecific and linked groups respectively. Other such materials can include the phenanthroline tetraacetic acid ligands which may be prepared using the process set forth in European patent application No. 0068875 (Eastman Kodak).

As representative specific embodiments of ligands which can participate in this metal transfer mechanism one can employ

| First or "Donating" Chelate | Second or "Receiving" Ligand |
|---|---|
| Rare earth metal chelate of triacid of the formula $$\begin{array}{c} HOOC-CH_2 \\ \phantom{HOOC-}\diagdown \\ \phantom{HOOC-CH_2}N-R-N \\ \phantom{HOOC-}\diagup \\ B-L-OC-CH_2 \end{array} \begin{array}{c} CH_2-COOH \\ \diagup \\ \phantom{N-R-}\diagdown \\ CH_2-COOH \end{array}$$ Wherein B is a biospecific molecule and L is a linking group as shown in U.S. Pat. No. 4,352,751 | Pyridine diacid |
| Rare earth metal chelate of the above triacid | Bis-dicarboxy alkyl amino alkyl pyridine or Pyridine diacid or Phenanthroline di-or tetraacid |
| Rare earth metal chelate of diethylene triamine tetraacetic acid (DTTA) | Same |
| Rare earth chelate of para-substituted phenyl EDTA acids | Same |

With the foregoind systems, the detected change could be an increase in fluorescence as the metal transfer takes place and the second chelate is formed.

| | |
|---|---|
| Cobalt or other metal complex of EDTA or DTTA or other | Pyridine diacid or Bis-dicarboxy alkyl amino alkyl pyridine or |
| aminopolycarboxylic acid | Phenanthroline di- and tetraacid |

With these systems, the detected change could be a change in spectral properties as the metal transfer takes place and the second chelate is formed.

The foregoing materials are representative. It is to be understood that the present invention is not dependent upon the use of any particular ligand or chelate but rather upon the use of an initial chelate and second chelate-forming ligand which will permit the desired physical transfer of the metal ion. It will also be appreciated that the choice of these materials will be made to obtain two materials having a measurable difference in properties so that the desired measurement can be effected.

The Biospecific Groups

As noted, the reporter mechanism of this invention comes into play in conjunction with a biospecific reaction and serves as an indication that this biospecific reaction takes place. In several or the embodiments of this invention, the initial chelate ligand can be attached to a biologically active, i.e., biospecific group. Likewise, the receiving or second ligand can be linked to a second biologically active group capable of reacting with the first biospecific group in some embodiments. The terms "biospecific group" and "biologically active group" are used in a broad sense to encompass all molecular structures which will "specifically recognize" or "specifically react" or "specifically interact" with another molecular species. Such groups can include immunologically specific groups such as antibodies and their respective antigens or haptens, hormones and their receptors, binding pairs such as the biotin/avidin pair and the like. They can also include nucleic acid sequences which will specifically hybridize with their complimentary sequences. The binding partners will be referred to generically from time to time as "antibody-like" and as "target-like" molecules.

The biospecific groups can be selected to bind with or otherwise associate with a target molecule or can be selected to mimic or to include the target molecule so as to compete with the target in the biospecific reaction.

It will be appreciated that to achieve the highest sensitivities it may be advantageous to purify the binding partners in terms of their biospecificity through application of affinity chromatography and like techniques.

The Links To The Biospecific Material

When the initial chelate is linked to a specific binding material, that is, one half of a biospecific (e.g., immunologic) pair or, likewise, the other chelate-forming ligand is linked to the other half of the specific-binding pair, this coupling can be through covalent chemical bonds or it can be an "antibody-antigen" type binding between the chelate or ligand and the specific binding material as is described in *Fluorescent Antibody Techniques and Their Application*, A. Kawamura, Ed., University Park Press, Baltimore, Md. 1969. The chelate-forming ligand moieties can be the site of linking to the biospecific groups. This linking can be accomplished by a direct covalent bond or through some other linking group either of which can constitute one of the R', R" or Rs, especially one of the Rs in the above described ligand structures of the initial chelate. When coupling a chelate, this will generally be carried out by attaching the ligand of the first chelate and then adding the metal ion to it.

When the linking is accomplished through a linking group this R group should present an active or bondable site such as an amine, a hydroxyl, a carboxyl, an ester or the like to facilitate coupling of the biospecific group. Examples of such bondable R groups are the amino group ($-NH_2$), primary and secondary amine-terminated alkyls, primary and secondary amine terminated aryls and aryloxies, and the isomers thereof and the like; hydroxyl-containing alkyls, and hydroxyl-containing aryls and aryloxies.

Other suitable functionalities for forming a bond to the biospecific group include amides, amidines, thioamides, ureas, thioureas, guanidines, diazos, thioethers, carboxy and phosphate esters and thioesters and other covalent linkages such as are known in the art. A preferred linking group is the simple amino group. The linking groups can couple directly to the biologically active group or can be linked through a bifunctional spacer agent such as a member of the group $)_4-$, $-CS-$, $-CO(CH_2)_8NHCOCH_2ON=$, $-COCH_2ON=$, $-CO(CH_2)_5NHCO(CH_2)_6CO-$, $-CO(CH_2)_2SS(CH_2)_2CO-$, $-CSNH(CH_2)_3N(CH_2CH_2)_2N(CH_2)_3NH-CO(CH_2)_6CO-$, $-CSNH(CH_2)_3N(CH_2CH_2)_2N(CH_2)_3NHCO(-CHOH)_2CO---CSNH(CH_2)_3N(CH_2CH_2)_2N(CH_2)_3NH-COCH_2ON=$ and the like. Such linking groups and spacer units are representative.

The Analyte Molecule

The analyte or target molecule which corresponds to or interacts with the biospecific group may be a monepitopic or polyepitopic material. It may be selected without limitation from materials such as drugs, metabolites, natural products, pesticides, chemicals and contaminants of air and water. For purposes of illustration, one can list drugs including digoxin, digitoxin, phenytoin, theophylline, gentamicin, and tobramycin; alkaloids such as morphine, heroin, cocaine, ergot alkaloids, and the like; steroids such as the steroid hormones including estrogens and androgens for example estriol and anti-inflammatory steroids for example cortisol; lactams such as the barbiturates including phenobarbital; aminoalkylbenzenes such as the amphetamines; vitamins, protaglandins such as $F_2$alpha and E, antibiotics and the like, short peptide sequences or amino acids such as thyroxine, triiodothyronine and oxytocin. Representative pollutants and pesticides include PCB, dioxin, halogenated biphenyls, carbamates, thiophosphites, phosphate esters and their metabolites. Such materials can range in molecular weight from about 50 to about 2000.

The target molecule can also be a polymeric material such as a protein or other polyamino acid, a polynucleic acid or a polysaccharide. Typical protein materials can be taken from any of the classes of proteins including without limitation globulins, albumins, lipoproteins, glycoproteins, histones and the like, hypersensitive proteins including albumin, the immunoglobulins such as IgE, fibrinogen, transferrin, the various complement factors, the tumor markers like CEA (carcinoebrionic antigen) and PAP, the various blood clotting factors and protein hormones including, beta-hCG, FSH, gastrin, LH and prolactin; insulin, thyrotropin, gonadotropin and the like. Examples of biospecific polysaccharides are those derived from microorganisms such as those associated with various species of Salmonella, Streptococcus, and Klebsiella. Other targets include without limitation materials responsive to infectious disease conditions such as infection with hepatitis or rubella.

The foregoing list is intended to be a brief outline. It is to be recognized that other equivalent materials such as are listed in more detail in the art (see, U.S. Pat. No. 4,193,983, columns 7-11 incorporated herein by reference) could be used in conjunction with the reporter mechanism provided by this invention.

Reporter Mechanism and Analysis Methodologies

This reporter mechanism involves a process in which, after a biospecific reaction takes place, a metal ion is transferred directly from a first chelate complex to a ligand to form a second chelate complex. The two complexes involved in the mechanism of this invention are separate and istinct from one another. This means that the ligands involved in the second complex are different from the ligands involved in the first complex. This transfer results in a change in the environment of the metal which is observed as a change in its measurable properties. In a particularly preferred embodiment, the metal ion is a rare earth metal ion and the properties which change and are measured are fluorescent properties as measured by application of the techniques of fluorescent background rejection set forth in U.S. Pat. No. 4,058,732.

It is known that metals can be transferred from one chelating group to another (Bates et al, J. BIOL. CHEM., 242:2810 (1967)), especially one with a higher binding constant and rate constants of the transfer process have been measured. In other studies (Margerum et al, J. AMER. CHEM. SOC., 87:4463 (1965)), the displacement of one metal from EDTA-type chelates by another metal having a higher binding constant was found to proceed in a stepwise fashion with the release of coordinating groups from the first metal being followed by their coordination to the second metal. This implies that for a finite period of time during the displacement, a ternary complex is formed with both metals. By analogy, with two ligands competing for a single metal, it is expected that a transitory ternary complex will be formed. This mechanism requires that there be actual transfer of the metal from one chelate into another. This is distinguishable from methods in the art wherein a metal is complexed, released from the complex into solution by a pH change or the like and then recomplexed with a second ligand, or from other methods in the art wherein a first complex is modified such as by the addition of activators, enhancers or flooders.

The reporter mechanism of this invention can be employed in the wide range of homogeneous and heterogeneous analysis methodologies known in the art which involve a biospecific reaction. These methodologies can involve competitive assay schemes or they can involve immunometric schemes.

A heterogeneous competitive assay (I) can be illustrated pictorially as:

Step 1.

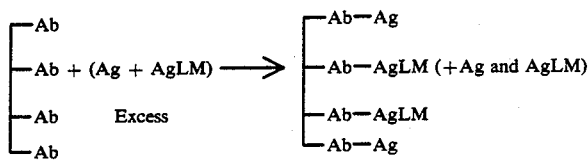

Step 2.
Seperate bound material from excess.

Step 3

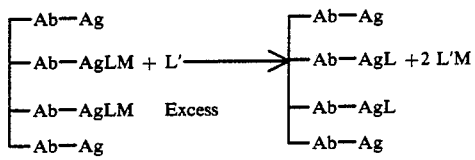

In this case, the first step involves a biospecific reaction. A test solution containing an analyte (shown as antigen "Ag") and an added labelled competitor of the analyte (shown as "AgLM", in which L is a ligand and M is a metal ion in complex combination with L) is contacted with a reaction-limiting amount of one or more biospecific binding sites on a second biospecific species shown as antibody (Ab) to the Ag and AgLM groups. This antibody is shown as a plurality of Ab's attached together to illustrate that it is physically separable from the test solution. This separability would be possible if the antibodies were attached to a solid, such as a bead, a test strip, a test tube wall or the like. The attachment of antibodies to solids has been well documented in the literature and can be effected, in the case of common plastics such as polystyrene merely by contacting the plastic with a solution of the antibodies sought to be bound. Many commerical antibody-on-solid preparations are available, as well. Other methods of achieving separablity such as by dialysis, or the like, could also be used, if desired.

The analyte in the test material and the added material which carries a first metal ion chelate compete for the antibodies thereby forming a separable biospecific reaction product. This reaction is usually carried out at ambient temperatures, although somewhat higher or lower temperatures, for example from about 5° C. to about 40° C. could be used if desired. This reaction is usually carried out in an aqueous medium and is usually complete within a minute or two to thirty minutes. (These general conditions will be referred to from time to time as biospecific reaction conditions.) The relative proportions of Ag, Ag-LM and Ab are set in this embodiment such that the number of molecules of Ag-LM equals or exceeds the number of molecules of Ab. Ideally to achieve good range and sensitivity the amount of Ag is from about 0.1 to about 10 times the amount of Ag-LM, although, of course, Ag being an unknown, could be lower than this range. Also, when setting these relative proportions, changes in affinity for the Ab between the Ag and AgLM must be taken into account so that true competition takes place. The absolute concentrations of these reactants can vary but generally are chosen such that the concentration of Ab-LM added to the test solution is from about $10^{-4}$ molar to about $10^{-15}$ molar.

In the second step, the biospecific reaction product is separated from the unreacted excess Ag and Ag-LM. This can be carried out by any method appropriate to the nature of the product. For example, if the product is a solid and the test solution is a liquid, this separation can be effected by pouring off the liquid and rinsing the solid of residual test liquid.

In the third step, the separated biospecific product is contacted with an excess of a second ligand (L') which can contact the chelate and bring about metal transfer from it to form a new different chelate (L'M). This contacting is preferably carried out in aqueous medium and at ambient conditions such as a temperature of 5° C. to about 40° C. for a period of from about one minute to about 30 minutes. The amount of L' added is from about 1.1 to about $10^6$ times the amount of M present on the sample and especially from about $10^3$ to about $10^6$ times, although larger excesses of L' may be used if desired.

The presence of the second chelate can be detected by appropriate methods depending upon the nature of the change between the two chelates. For example, by the use of a spectrophotometer for spectral changes or by means of a fluorometer for fluorescence changes. As previously noted, it is much preferred, in the case of fluorescence measurements to employ background rejection methods in determining these changes.

Finally, the detected presence of the second metal ion chelate is related to the presence of the analyte in the test sample. This can be a qualitative measurement in which only the presence or absence of the analyte is sought or it can be a quantitative measurement in which the amount of analyte in the test sample is determined. This determination is generally made by comparing the noted change with changes noted with known materials. In this particular method, since the amount of Ag-LM coupling to the Ab will be inversely related to the amount of Ag in the test sample, the magnitude of the measured change will be inversely proportional to the level of Ag.

Alternative heterogeneous competitive assay methodologies are possible, as well. For example, an excess of soluble Ag and separable Ag could compete for a limited amount of soluble added antibody (Ab). This method (IA) could be represented as follows:

Step 1.

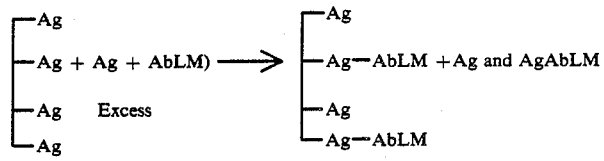

Step 2.
Seperate bound material from excess.

Step 3

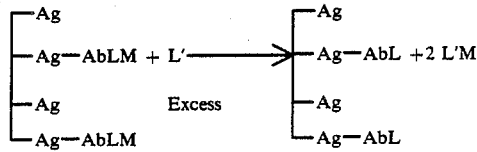

This case would be carried out in substantially the same manner as just described using the same general conditions and methods.

A heterogeneous immunometric assay (II) employing the present reporter mechanism can be illustrated pictorially as:

Step 1.

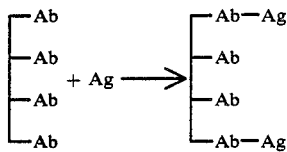

Step 2

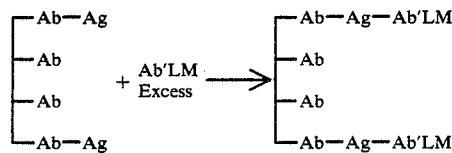

Step 3.

Separate bound material from excess.

Step 4

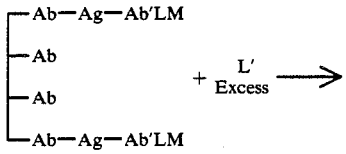

In this case, the first step involves
a. contacting the test material with an excess of a biospecific partner (Ab) for the analyte (Ag), thereby biospecifically coupling any analyte present in the test sample to form a first biospecific pair. As shown, the couple for the analyte is in a separable form such as by being insolubilized by being bound to a solid or the like. The usual biospecific reaction conditions can be employed.

In the second step the biospecific pair is contacted with a second biospecific partner for the analyte (Ab') which partner carries a first metal ion chelate (LM) thereby forming a first metal ion chelate-labeled biospecific trio (-Ab-Ag-AbLM). This reaction can be carried out using the conditions and excesses described with reference to Method (I) above.

The third step involves separating the biospecific trio from unreacted second biospecific partner by a method consistent with the nature of the separable form of Ab.

In the fourth step, the separated biospecific trio is contacted with an excess of a second ligand (L') which directly removes metal ion from the first metal ion chelate and forms a second metal ion chelate which is separate from and detectably different than the first metal ion chelate and the metal ion-containing biospecific trio.

The presence of the second metal ion chelate is then detected and this detected presence is related to the presence of the analyte in the test sample. In this analysis format, the amount of second chelate detected will be a direct function of the amount of analyte in the test sample such that the larger the amount of second chelate, the larger the amount of analyte in the test sample.

A homogeneous competitive assay (III) can be illustrated pictorially as:

Step 1.

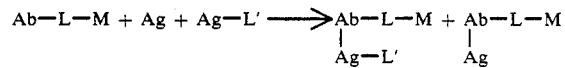

Step 2.
Incubate

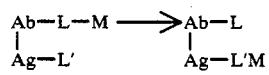

In this case, the first step involves a biospecific reaction. A test solution containing an analyte (shown as antigen "Ag") and an added labelled competitor of the analyte (shown as "AgL'", in which L' is a ligand capable of entering into complex combination with a metal (M) is contacted with a reaction-limiting amount of biospecific species shown as antibody (Ab) to the Ag and AgL' groups. This antibody (Ab) is attached to metal chelate (LM) in which L is different from L'. Ab-LM reacts biospecifically with both the Ag's in the sample and the AgLM's which have been added. This reaction is usually carried out at ambient temperatures, although somewhat higher or lower temperatures, for example from about 5° C. to about 40° C. could be used if desired. This reaction is usually carried out in an aqueous medium and is usually complete in within a minute or two to thirty minutes, i.e. at the general biospecific reaction conditions. The relative proportions of Ag, Ag-L' and Ab-LM are set in this embodiment such that the number of molecules of Ag-L' equals or exceeds the number of molecules of Ab-LM. If excess AbLM were present, in theory all the Ag-L' would react such that no competition between the Ag and Ag-L' would be noted. Generally to achieve good range and sensitivity the amount of Ag is from about 0.1 to about 10 times the amount of Ag-L', although, of course, Ag being an unknown, could be lower than this range. Again, when setting proportions, changes in affinity should be taken into account to assure true competition. The absolute concentrations of these reactants can vary but generally are chosen such that the concentration of Ab-LM added to the test solution is from about $10^{-4}$ molar to about $10^{-15}$ molar.

In the second step, the biospecific reaction product is incubated. This permits the metal ion M to be exchanged or transferred directly from the L ligand to the L' ligand, thereby giving rise to a new chelate which is different from the original chelate. This incubation is preferably carried out in aqueous medium and at ambient conditions such as a temperature of 5° C. to about 40° C. for a period of from about one minute to about 30 minutes.

The presence of the second chelate can be detected by appropriate methods depending upon the nature of the change between the two chelates. For example, by the use of a spectrophotometer for spectral changes or by means of a fluorometer for fluorescence changes. As previously noted, it is much preferred, in the case of fluorescence measurements to employ background rejection methods in determining these changes.

Finally, the detected presence of the second metal ion chelate is related to the presence of the analyte in the test sample. This can be a qualitative measurement in which only the presence or absence of the analyte is sought or it can be a quantitative measurement in which the amount of analyte in the test sample is determined. This determination is generally made by comparing the noted change with changes noted with known materials. In this particular method, since the amount of Ag-LM coupling to the Ab will be inversely related to the amount of Ag in the test sample, the magnitude of the measured change will be inversely proportional to the level of Ag.

In a variation of the homogeneous competitive analysis just depicted the labelled antigen can carry the metal and the antibody can carry the receiving ligand. This analysis mechanism (IIIA) can be depicted pictorially as Step 1.

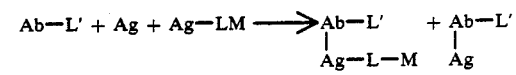

Step 2.
Incubate

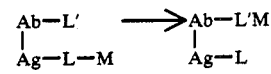

The same general reaction conditions are employed with the relative proportion of added antigen and antibody being controlled to achieve competition between the antigen in the test sample and the added antigen for a limited amount of antibody.

While, as shown by analysis sequences III and IIIA, either the starting chelate (LM) and the receiving ligand (L') may be coupled to either member of the binding pair, in preferred embodiments the first chelate (LM) is coupled to the target-like molecules (Ag) and forms the initial chelates while the second ligand (L') is coupled to the antibody-like molecules. Small target-like molecules will generally be coupled to a single first ligand, although larger analytes may be multiply labeled. The antibody-like molecules will generally be labeled with several second ligands.

At the concentrations used in immunoassays (on the order of $10^{-8}$ M or less) transfer of the metal from the first ligand to the second ligand would be a very slow process in the absence of a specific binding reaction between the member of the binding pair. Indeed, a specific pair of first and second ligands not coupled to target-like or antibody-like molecules were found to require many hours for detectable metal transfer to occur at $10^{-9}$ M where transfer is dependent on diffusion and random collisions, while at $10^{-5}$ M and higher concentrations, transfers of metal occurred rapidly. Thus, in an assay for the target analyte, the specific binding reaction of the first chelate-labeled target-like molecule to the second chelate-labeled antibody-like molecule creates a locally high effective concentration leading to transfer of the metal to the second chelate and the accompanying increase in the measured property.

A homogenous immunometric assay (IV) can be represented pictorially as follows:

Step 1.

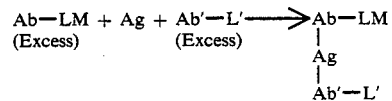

Step 2.
Incubate

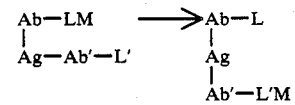

Thereafter the analysis is completed by detecting a change which results from the interligand transfer of the metal ion, relating the detected change to the extent of the biospecific reaction in step 1, and relating the extent of the biospecific reaction to the presence of the antigenic species. This will be a direct measurement with the amount of change in signal detected being directly related to the amount of antigen in the test sample.

In this assay, an excess of each of the antibody-like species is employed. The two antibody-like materials (Ab and Ab') are admixed with the test material which contains the antigen (Ag) simultaneously. Typical use levels for the two antibody-like materials are from about 1.1 to about 10 times the level of Ag. Although, as previously noted, since Ag is an unknown, its level may be zero so that the amount of the antibody-like species may be substantially greater than 10 times this level. The biospecific reaction in Step 1 is carried out at the usual biospecific reaction conditions. The incubation is carried out at the incubation conditions sufficient to effect direct interligand transfer of metal ion from the original metal ion chelate complex to the ligand thereby forming a second metal ion chelate complex as previously described, as well.

Several points bear noting with this embodiment (IV) of the invention. One is that in this embodiment, the final product contains the product of the interligand metal transfer but also contains unreacted first chelate. This means that the first material will be available to interfere with the signal given by the second chelate. If the second material is characterized as a material of increased properties, e.g. a material having an increased fluorescence this change will be detectable, not withstanding the interference. If it is a decreased property, such as a decrease in fluorescence, this will be somewhat more difficult to accurately detect in light of the interference. For this reason changes which present an increase in the property are preferred.

With the homogeneous assay embodiments of this invention, the ligand (L') on the second biospecific species (Ab' or AgLM) is positioned in such proximity to the biospecific couple that as a result of the biospecific reaction the ligand (L') can contact and react with the metal ion chelate complex (LM) carried by the first species (Ab).

In the homogeneous settings, the occurrence of the biospecific reaction brings the two ligands into such close proximity with one another that the direct transfer of the metal ion from one chelate structure to the other can take place thus imposing the requirement in this embodiment that the linking group or functionalities coupling each of the ligands to its respective member of the binding pair be sufficiently long and flexible to allow contact of the two ligands once the binding reaction has taken place.

In this mechanism, the second ligand (L'), that is the receiving ligand, should have the property of forming a complex with the metal ion (M) which has an approximately equal or higher level of stability than does the complex with the first, or donating, ligand (L).

The reporter mechanism of the present invention and its use in analysis settings will be further illustrated by the following examples. These are provided as illustrations and are not to be construed as limitations on the scope of the invention as defined by the appended claims. In these examples, metric measures are employed unless otherwise specified.

EXAMPLE I

Thyroxine Fluoroimmuoassays

A. Preparation of L-Thyroxine-N-[4-(4-Isothiocyanatobenzyl)-1, 4, 7-triazaheptane]-1,1,7,7-tetraacetic Acid (T4-ITC-Benzyl-DTTA, Structure 3, Sequence 1).

To a solution of the isothiocyanate 2 shown in Reaction Sequence 1 (74 mg, 0.137 mmole) in methylene chloride (1 mL) was added the T4 methyl ester hydrochloride 1 (113 mg, 1.137 mmole) in DMF (1 mL containing triethylamine (50 uL) for formation of the free amine. After stirring 2 hours at room temperature the mixture was diluted with chloroform and washed with water, 1% citric acid and again with water. The chloroform extract was dried over sodium sulfate, filtered and evaporated. The crude residue was plug filtered through silica gel with 5% methanol/ethyl acetate to give the pentamethyl ester of 3 (73 mg, 40% yield, tlc Rf=0.7 on silica gel with 5% methanol/ethyl acetate, NMR consistent with assigned structure). This material was then dissolved in 3 mL of methanol containing three drops of THF. To this solution was added water (1.5 mL) followed by potassium carbonate (150 mg). The resulting mixture was stirred overnight at room temperature, acidified with 1N HCl to pH 3 and evaporated to dryness on the rotary evaporator. The solid residue was extracted several times with ethanol, the extracts combined and the solvent removed to give the desired pentaacid 3 (53 mg, 78% yield, IR 3420 (—OH), 2960 (C—H), 1730 (C=O) cm-1, Rf=0.9 on C-18 reverse phase silica gel with methanol:water, 70:30).

B. Total T4 Fluroimmunoassay

The components of a commercial T4 immunoassay kit (Clinical Assays GAMMACOAT [125-I] Free/Total T4 Radioimmunoassay Kit), including T4 serum blank and standards (0,1,4,8,12, and 20 ug/dL) and rabbit anti-T4 serum coated tubes, were used to prepare a standard curve. The [125-I]-T4 tracer was replaced with the T4 analog 3 from Example I.A above having a terbium ion chelated thereto. Duplicate tubes were labeled for each standard and the serum blank and 10 uL of the appropriate samples were added to each tube followed by 1 mL of $3 \times 10^{-9}$M tracer in pH 7.4 Tris buffered saline containing $4 \times 10^{-4}$M 8-anilino-1-naphthalenesulfonic acid (ANS). The tubes were gently vortexed and incubated at room temperature for 45 minutes. All tubes were then aspirated and rinsed with $4 \times 1$ mL distilled water. The diacid (1.25 mL of 0.1 m pH 6 sodium borate containing $3 \times 10^{-5}$M 4-(2,4,6-trimethoxyphenyl)-pyridine-2,6-dicarboxylic acid prepared in accord with the teachings of Example I.B. of U.S. patent application Ser. No. 712,774 (incorporated herein by reference) was then added to each tube and the tubes incubated at room temperature for 30 minutes. Results are given in Table 1 and shown graphically in FIG. 1.

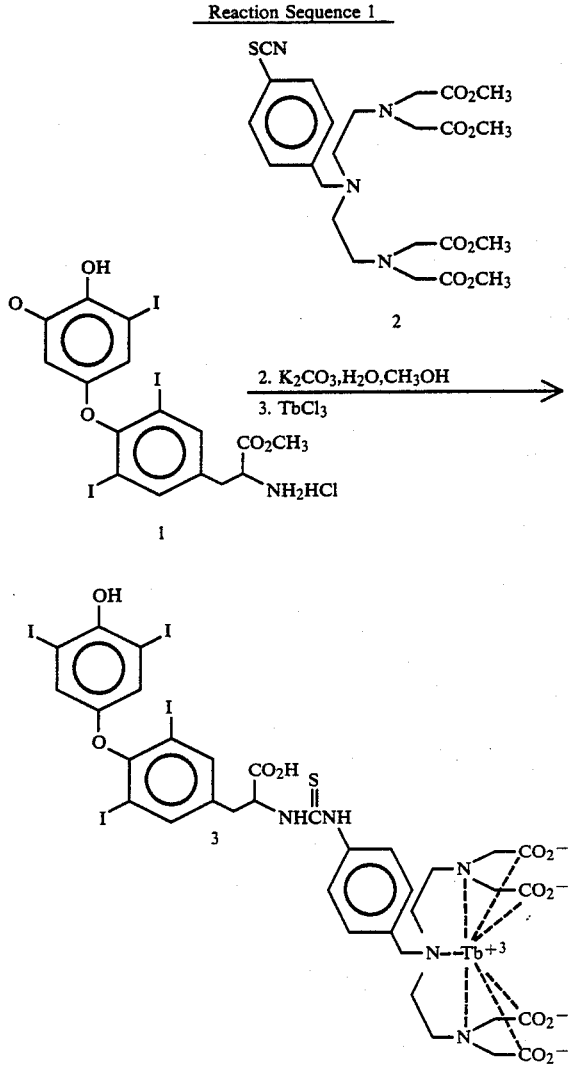

Reaction Sequence 1

C. Free T4 Fluoroimmunoassay

Figure 2:
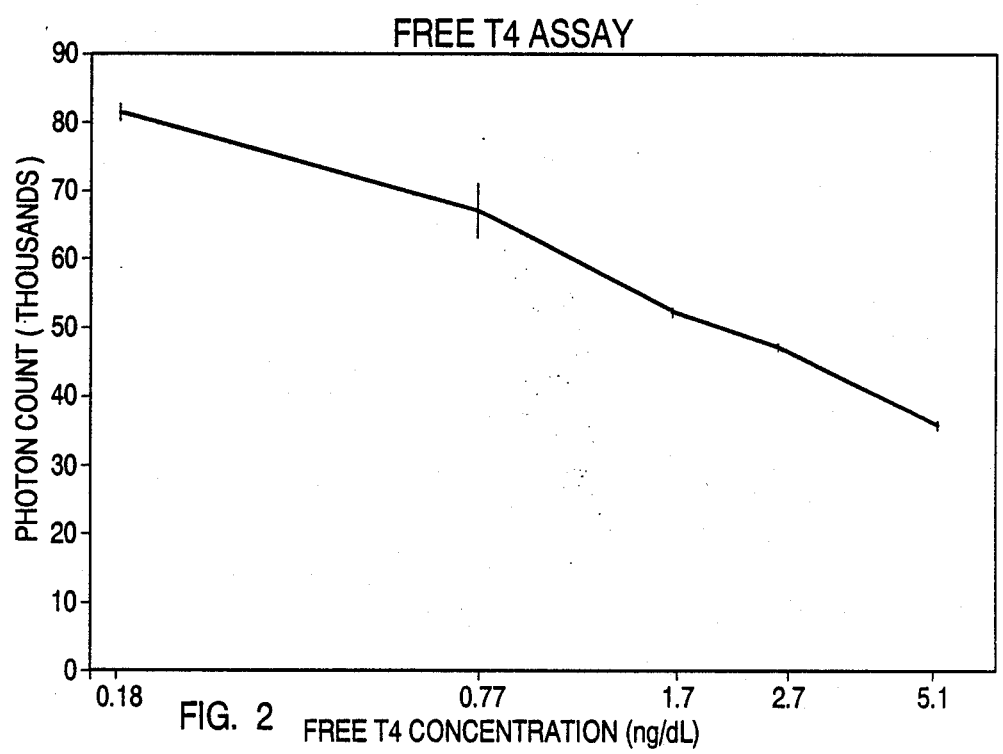

A modified one-step GAMMACOAT procedure for free T4 was used with the components from the kit described in Example I.B. above. The free T4 serum blank and standards contained 0, 0.18, 0.77, 1.7, 2.7, and 5.1 ng/dL. To the bottom of appropriately labeled duplicate tubes was added 50 uL of blank or standard and 1 mL of the above T4-Tb chelate tracer 3 solution from which the ANS had been omitted. The tubes were vortexed gently and incubated at 37C for 90 minutes and then aspirated and rinsed with 4×1 mL of distilled water. The diacid solution (1.25 mL) of Example I.B. was then added and the tubes incubated for one hour at room temperature. The fluorescence of the solution was then measured as above and the results of the fluorescence measurements used to provide an assay for T4. These results are given in Table 2 and FIG. 2.

EXAMPLE II

Triiodothyronine Fluoroimmunoassays

A. Preparation of Triiodothyronine-N-[4-(4-isothiocyanatobenzyl)-1,4,7-triazaheptane]-1,1,7,7-tetraacetic Acid (T3-ITC-Benzyl-DTTA, Structure 5, Reaction Sequence 2)

This preparation was performed in the same manner as that of the T4 analog 3 employing the isothiocyanate 2 (441 mg, 0.82 mmole) and 3,3,5-triiodo-L-thyronine 4 (534 mg, 0.82 mmole) with triethylamine (114 uL, 0.82 mmole). The yield was 231 mg (24%) of the tetramethyl ester. Saponification was done with lithium hydroxide rather than potassium carbonate. The IR was barely distinguishable from the T4 analog and the TLC (C-18 reverse phase silica gel with methanol:water, 70:30) gave a single spot with Rf=0.87.

B. T3 Fluoroimmunoassay

Figure 3:
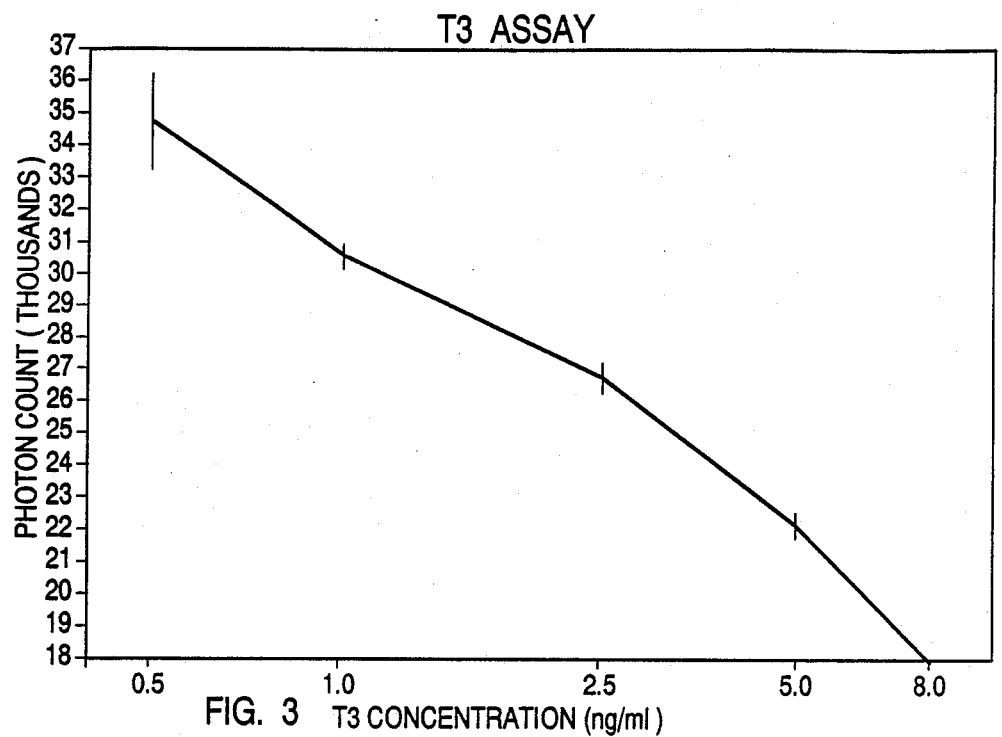

The components of a commercial T3 immunoassay kit (Clinical Assays GAMMACOAT [125-I] T3 Radioimmunoassay Kit), including T3 serum blank and standards (0, 0.5, 1.0, 2.5, 5.0, and 8.0 ng/mL), and rabbit anti-T3 serum coated tubes, were used to prepare a standard curve. The [125-I]-T3 tracer was replaced with the T3 analog 5 from Example II.A. above having a terbium ion chelated thereto. Duplicate tubes were labeled for each standard and the serum blank and 50 uL of the appropriate samples were added to each tube followed by 1 mL of $3 \times 10^{-10}$M tracer in pH 7.4 Tris buffered saline containing $4 \times 10^{-4}$M ANS. The tubes were gently vortexed and incubated at 37C for one hour. All tubes were then aspirated and rinsed with $4 \times 1$ mL distilled water. The diacid (1.25 mL of 0.01M pH 6 sodium borate containing $3 \times 10^{-5}$M 4-(2,4,6-trimethoxphenyl)-pyridine-2,6-dicarboxylic acid) was then added to each tube and the tubes incubated at room temperature for one hour. The fluorescence of the solution was then measured as above and the results are given in Table 3 and FIG. 3.

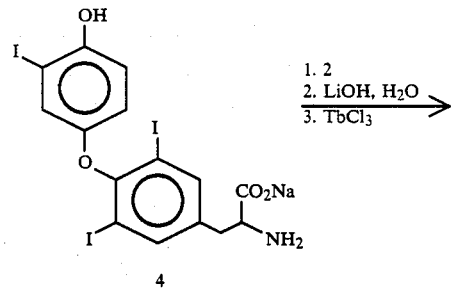

Reaction Sequence 2

-continued
Reaction Sequence 2

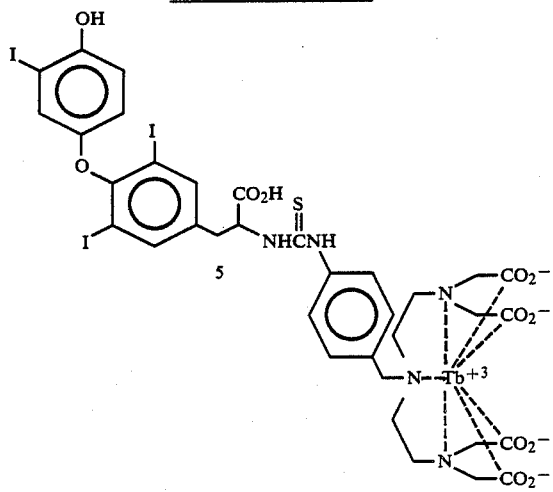

TABLE 1

| STANDARD | CPS | MEAN | % B/Bo | C.V. |
|---|---|---|---|---|
| TOTAL T4 ASSAY | | | | |
| 0 ug/dl | 149495 | | | |
| | 137081 | 143288 | | 4.3% |
| 1 ug/dl | 147092 | | | |
| | 129979 | 138535.5 | 96.7% | 6.2% |
| 4 ug/dl | 101150 | | | |
| | 93740 | 97445 | 68.0% | 3.8% |
| 8 ug/dl | 87259 | | | |
| | 83286 | 85272.5 | 59.5% | 2.3% |
| 12 ug/dl | 72721 | | | |
| | 72721 | 72721 | 50.8% | 0.0% |
| 20 ug/dl | 63213 | | | |
| | 70644 | 66928.5 | 46.7% | 5.6% |

TABLE 2

| STANDARD | CPS | MEAN | % B/Bo | C.V. |
|---|---|---|---|---|
| FREE T4 ASSAY | | | | |
| 0 ng/dL | 90014 | | | |
| | 85207 | 87610.5 | | 2.7% |
| 0.18 ng/dL | 81757 | | | |
| | 79363 | 80560 | 92.0% | 1.5% |
| 0.77 ng/dL | 71757 | | | |
| | 62675 | 67216 | 76.7% | 6.8% |
| 1.7 ng/dL | 52561 | | | |
| | 51916 | 52238.5 | 59.6% | 0.6% |
| 2.7 ng/dL | 47561 | | | |
| | 46679 | 47120 | 53.8% | 0.9% |
| 5.1 ng/dL | 36431 | | | |
| | 35942 | 36186.5 | 41.3% | 0.7% |

TABLE 3

| STANDARD | CPS | MEAN | % B/Bo | C.V. |
|---|---|---|---|---|
| T3 ASSAY | | | | |
| 0 ng/ml | 35337 | | | |
| | 34142 | 34730.5 | | 1.7% |
| 0.5 ng/ml | 36343 | | | |
| | 33062 | 34702.5 | 99.9% | 4.7% |
| 1.07 ng/ml | 31214 | | | |
| | 29930 | 30572 | 88.0% | 2.1% |
| 2.5 ng/ml | 27484 | | | |
| | 26452 | 26968 | 77.6% | 1.9% |
| 5.0 ng/ml | 21886 | | | |
| | 22886 | 22386 | 64.5% | 2.2% |
| 8.0 ng/ml | 18225 | | | |
| | 18102 | 18163.5 | 52.3% | 0.3% |

EXAMPLE III

Cortisol Fluoroimmunoassays

A. Preparation of Cortisol-3-(0-carboxymethyl)oxime (6-t-BOC-amino)hex -1-amide (2, Reaction Sequence 3)

Cortisol-3-CMO (1 (Reaction Sequence 3), 349 mg, 0.8 mmole), 1-hydroxybenzotriazole (115 mg, 0.85 mmole) and 1-ethyl- 3,3-dimethylaminopropyl carbodiimide hydrochloride (192 mg, 1.0 mmole) were added to pyridine (2 mL) and the mixture stirred at room temperature for one hour. 1-(N-tBOC-amino)-6-aminohexane (194 mg, 0.9 mmole) in pyridine (0.3 mL) was added and stirring continued for three hours. Additional carbodiimide (160 mg, 0.83 mmole) was then added and stirring continued for another two hours. Thin-layer chromatography (silica gel, chloroform:methanol 9:1) indicated all of the cortisol-3-CMO (Rf=0.03) had reacted to give a mixture of the syn and anti isomers of 2 9Rf0.65 and 0.60). The reaction solvent was removed on a rotary evaporator at 45° C. and the thick oily residue was partitioned between ethyl acetate containing 5% methanol (30 mL) and water (20 mL). The organic layer was washed with 1% aqueous citric acid and water and dried and evaporated to give the crude product (500 mg). The material was dissolved in 10% methanol in chloroform and filtered through a plug of silica gel (3 g). Evaporation of solvent gave 478 mg (0.75 mmole, 94% yield) of 2 as a white solid (m.p. 178C (dec), NMR consistent with structure).

B. Preparation of Amine 3

The t-BOC protected amine 2 (400 mg, 0.63 mmole) from above was deprotected by treatment with a mixture of trifluoroacetic acid and methylene chloride (1:6 volume, 4 mL) at room temperature for three and one-half hours. Thin-layer chromatography (silica gel, chloroform:methanol 9:11) showed no starting material remaining with the product at the origin. The reaction mixture was then concentrated on the rotary evaporator and the residue triturated with ethyl ether to give the product 3 as a solid (370 mg, 0.57 mmole, 90.4% yield, m.p. 150–168° C.(dec). The IR and NMR spectra showed the disappearance of the t-butyl group in agreement with the structure.

C. Preparation of Cortisol-3-CMO-C6-DTPA (5, Reaction Sequence 3)

The symmetrical mono p-nitrophenyl active ester of DTPA (4, 120 mg, 0.233 mmole) was added to a dimethylformamide solution (1.5 mL) of amine salt 3 (150 mg, 0.233 mmole) and triethylamine (0.22 mL, 1.58 mmole) and the resulting yellow solution was stirred overnight at room temperature. The solvents were removed by evaporation to give a viscous oil which was triturated with ethyl acetate to give a solid which was removed by filtration and washed with ethyl acetate (2×15 mL). The solid was then resuspended in warm ethanol (15 mL), cooled to room temperature and separated by centrifugation to give, after drying, 130 mg of crude product. This material was redissolved in aqueous potassium carbonate (62 mg in 3 mL) and the solution was acidified with 1N HCl to pH 2 to give a precipitate which was isolated by centrifugation. This material was further desalted by resuspending it in methanol (15 mL) and removing the insolubles by filtration. The filtrate was concentrated and reprecipitated by addition of ether to give the desired product 5 (44 mg, 0.048 mmole, 20.7% yield).

D. Cortisol Assay

Figure 4:
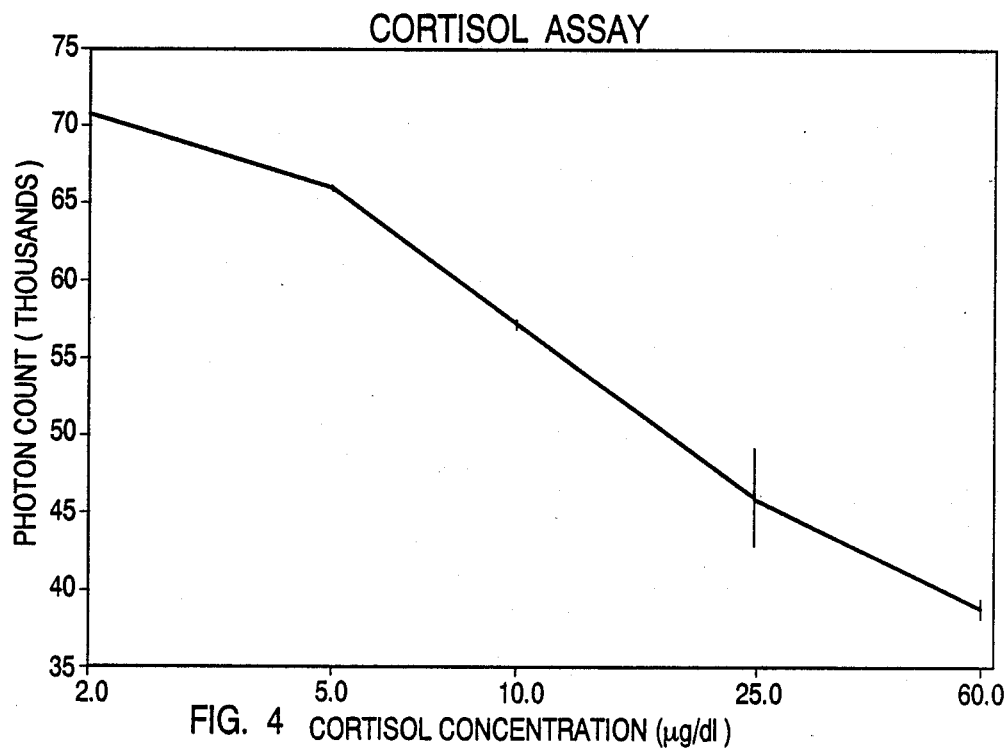

A standard curve was prepared using cortisol serum blank and standards (0,2,5,10,25, and 60 ug/dL) and rabbit anti-cortisol serum coated polystyrene cups. The tracer used was the cortisol analog 5 from Example III.C. above chelated to one equivalent of terbium. Duplicate tubes were labeled for each standard and the serum blank and 10 uL of the appropriate samples were added to each tube followed by 1 mL of $10^{-9}$M tracer in pH 7.4 Tris buffered saline containing $2 \times 10^{-4}$M ANS. The tubes were gently vortexed and incubated at 37° C. for 45 minutes. All tubes were then aspirated and rinsed with $4 \times 1.5$ mL distilled water. The diacid (1.25 mL of 0.01M pH 6 sodium borate containing $3 \times 10^{-5}$M 4-(2,4,6trimethoxyphenyl)-pyridine-2,6-dicarboxylic acid) was then added to each tube and the tubes incubated at room temperature for one hour. The fluorescence of the solution was then measured as above and the results are given in Table 4 and FIG. 4.

TABLE 4

| STANDARD | CORTISOL ASSAY | | | |
|---|---|---|---|---|
| | CPS | MEAN | % B/Bo | C.V. |
| 0 ug/dl | 91895 | | | |
| | 94415 | 93155 | | 1.4% |
| 2 ug/dl | 68700 | | | |
| | 72708 | 70704 | 75.9% | 2.8% |
| 5 ug/dl | 66181 | | | |
| | 65564 | 65872.5 | 70.7% | 0.5% |
| 10 ug/dl | 57432 | | | |
| | 56588 | 57010 | 61.2% | 0.7% |
| 25 ug/dl | 49494 | | | |
| | 42257 | 45875.5 | 49.2% | 7.9% |
| 60 ug/dl | 39513 | | | |
| | 37972 | 38742.5 | 41.6% | 2.0% |

Reaction Sequence 3

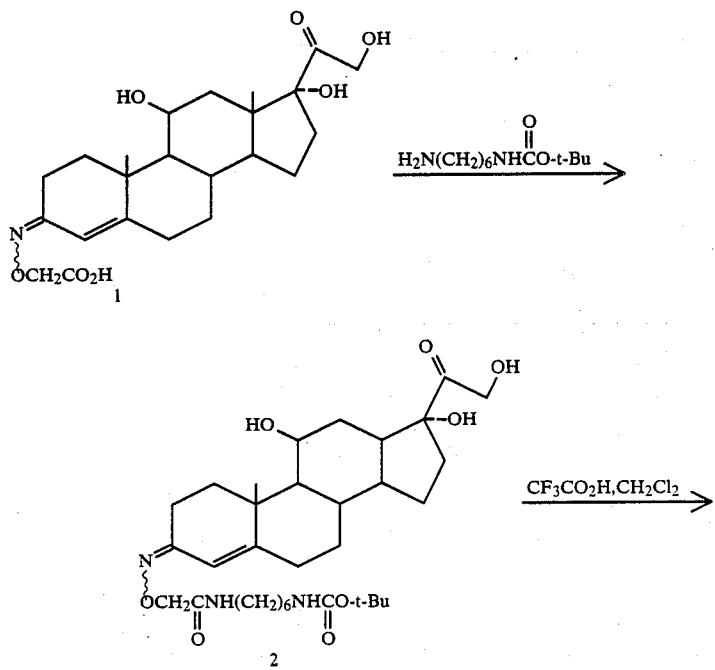

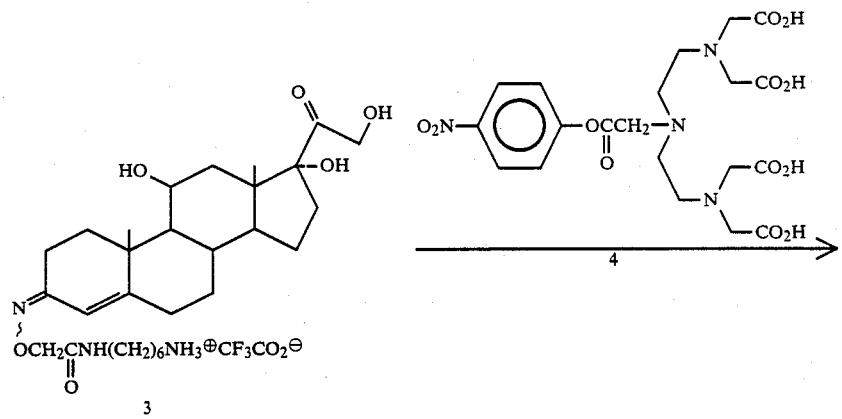

-continued

Reaction Sequence 3

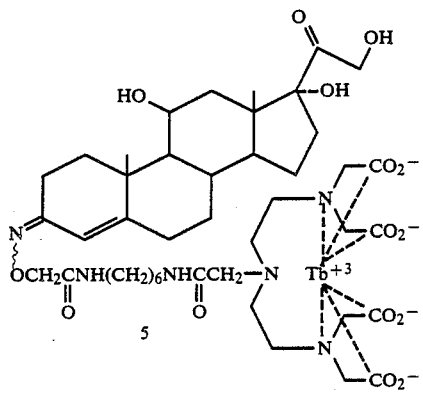

EXAMPLE IV

Theophylline Homogeneous Assays

A. Preparation of a Theophylline-linked Triacid First Chelate (Reaction Sequence 4)

Following the reaction scheme shown in Reaction Sequence 4 below, theophylline-8-butyric acid (10, 210 mg. 0.79 mmole) is dissolved in dimethylformamide (DMF, 8 ml) and the solution cooled in an ice bath to 0° C. Triethylamine (72.6 mg, 0.72 mmole) is then added, followed by isobutyl chloroformate (95 mg, 0.69 mmole) and the solution is stirred at 0° C. for 30 minutes during which time a white precipitate forms and intermediate mixed anhydride 11 is produced. Ethylenediamine (620 mg, 10.3 mmole) is added to give a clear solution which is stored overnight at 0° C. The mixture is then concentrated on a rotary evaporator at 70°-80° C. and the residue is triturated with diethyl ether. The resulting oily solid residue is recrystallized from ethanol to give 160 mg (0.52 mmole, 75% yield) of theophylline derivative 12, m.p. 199°-201° C.(dec.).

12 (155 mg, 0.51 mmole) and ethylenediaminetetraacetic acid dianhydride (13, 300 mg, 1.17 mmole) are dissolved in DMF (10 ml) and heated at 65° C. for 3 hours. Water (1.5 ml) is then added and heating continued for 1.5 hours followed by cooling at 0° C. The precipitate (EDTA, 134 mg) which forms is removed by filtration and the filtrate is concentrated on the rotary evaporator. The residual syrupy oil is triturated with acetone (40 ml) and the resulting solid is twice recrystallized from ethanol (40 ml) to give 119 mg (0.2 mmole, 40% yield) of the theophylline-linked triacid chelate 14a (m.p. ~130°-160° C., dec.). Similarly, homologs 14b and 14c, are prepared from 1.6-diaminohexane and 1,10-diaminodecane.

In addition, other analogs are prepared by use of such diamine linking groups as bis-2-aminoethyl ether, 1,2-bis(2-aminoethoxy)ethane and N.N-bis(3-amino propyl)piperazine.

Reaction Sequences 4 and 5

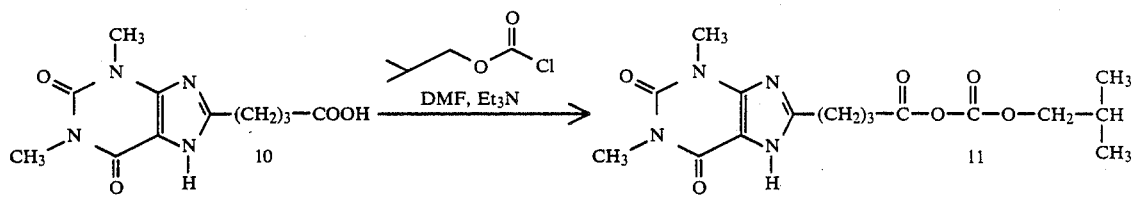

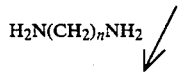

-continued
Reaction Sequences 4 and 5

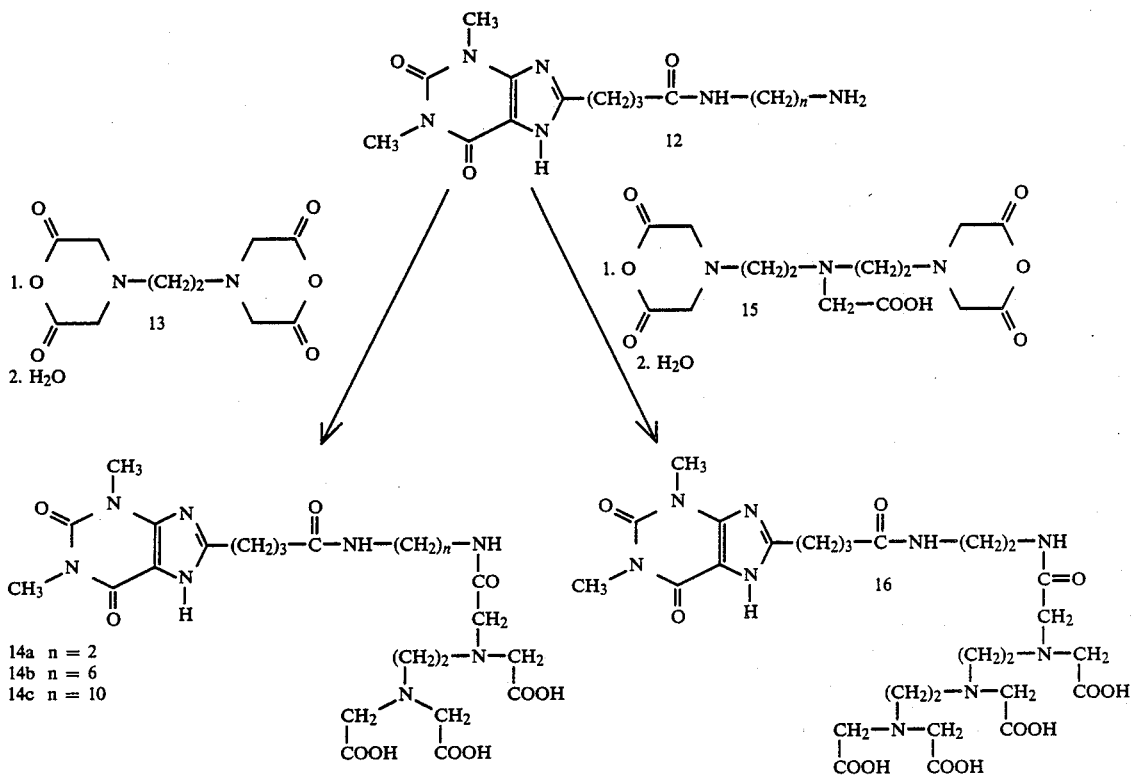

B. Preparation of Theophylline-linked Tetraacid First Chelate (Sequence 5)

Following the reaction scheme set forth in Reaction Sequence 5, above, intermediate 12 (164 mg. 0.53 mmole) is dissolved in DMF (3 ml) and slowly added to a stirred solution of diethylenetriaminepentaacetic dianhydride 15 in DMF (5 ml) and heated at 65° C. for 2 hours. After two hours, TLC indicates the disappearance of 12 and water (1.0 ml) is then added and heating continued for 40 minutes. After cooling to room temperature overnight a precipitate (DTPA, 220 mg) which forms is removed by filtration and the filtrate is concentrated on a rotary evaporator. The viscous residue is triturated with acetone. The resulting solid partially dissolves in hot ethanol. Additional DTPA is removed and the filtrate is cooled to crystallize the desired product 16. Addition of diethyl ether to the filtrate gives a second crop of solid. Total yield 190 mg, m.p. 129°-160° C., decomposition with loss of carbon dioxide.

C. Preparation of Antibody-linked Second Ligands

Four such ligands are prepared as shown in (1), (2), (3) and (4) respectively. Each of these preparations begins with an amino tetraester starting material.

This starting material can be prepared as set forth in a. through j. below:

a. 1,5-di(2-furyl)-3-phenyl-1,5-pentanedione

| Benzaldehyde | 62.6 g (60 ml) (0.59 mols) |
| 2-Acetyl furan, 85% | 165 g (150 ml) (1.27 mols) |
| Potassium hydroxide, 85% | 35 g (0.53 mols) | are reacted at 60° C. Following reaction, product crystals are recovered. Yield of pentanedione, 103.5 gms or 57.3%.

b. 4-Phenyl-2,6-di(2-furyl)pyridine

| 1,5-Di(2-furyl)-3-phenyl-1,5-Pentanedione | 143 g |
| Hydroxylamine hydrochloride | 129 g Aldrich 102337 |
| n-Butanol | 1600 ml Sigma 13F-5070 |

The "dione", as produced in step a, the hydroxylamine and the butanol are combined, refluxed and stirred, cooled and stirred for about 60 hours. The resulting black solution is worked up to yield about 79 g of product crystals.

c. 4-Phenyl-2,6-pyridinedicarboxylic acid

The difuryl pyridine product of step b. is oxidized with permanganate.

| Product of Step b | 23 mmoles |
| KMnO4 | 45.4 grams |
| t-Butanol | 1500 ml |
| Water | 300 ml |

The product of step b is added to the t-butanol. The mixture is heated and stirred then the H2O is added and the KMnO4 is added in portions over about 30 minutes at 75° C. The mixture is refluxed for 90 minutes. The product is worked up to give crystals of the desired 4-phenyl-2,6-pyridinedicarboxylic acid. The dicarboxylic acid which results is useful in its own right in the present invention as a ligand.

d. 4-Phenyl-2,6-pyridinedicarboxamide

| | |
|---|---|
| 4-Phenyl-2,6-pyridine-dicarboxylic acid | 21.5 mmoles |
| Oxalyl chloride | 4.8 ml |
| Methylene chloride | 80 ml |
| Dimethylformamide | 5 drops |

The pyridinedicarboxylic acid is added to the CH$_2$Cl$_2$, and DMF. The flask is closed with a CaSO$_4$ drying tube, and cooled in ice. The oxalyl chloride is added gradually. The resulting solution is concentrated and added to NH$_4$OH, 28%, over 5–10 minutes with stirring, stirred for an hour, filtered and washed with water and dried to give the desired amide.

e. 4-Phenyl-2,6-pyridinedicarbonitrile

| | |
|---|---|
| 4-Phenyl-2,6-pyridine-dicarboxamide | 17.5 mmoles |
| p-Dioxane | 170 mls |
| Pyridine | 11.3 ml |
| Trifluoroacetic anhydride | 11.0 ml |

The first three ingredients are combined and cooled to 10° C. The anhydride is added and the mixture is stirred for two hours at room temperature. The resulting dark solution is worked up to give the desired dicarbonitrile.

f. 4-Phenyl-2,6-di(aminomethyl)-pyridine

| | |
|---|---|
| 4-Phenyl-2,6-pyridine-dicarbonitrile | 13.5 mmoles |
| Ethanol with 2% HClO$_4$ | 370 ml |
| 10% Palladium on carbon | 3.7 g |

The nitrile is suspended in the ethanol and HClO$_4$. The catalyst is added and the system is then pressured to 40 psi with hydrogen. After 30 minutes a yellow solid is recovered by precipitation and dissolved in water and NaOH. The liberated amine that results is recovered as a dark oil.

g. 4-Phenyl-2,6-bis[N,N-di(methoxycarbonylmethyl)aminomethyl]-pyridine

| | |
|---|---|
| Amine of Step f | 12.0 mmole |
| 1,8-Bis(dimethylamino)-napthalene | 10.3 g |
| Methyl bromoacetate | 7.35 g |
| Acetonitrile | 130 ml |

The base, amine and acetonitrile are stirred. Then the methyl bromoacetate is dripped in. After about 16 hours at about 45° C., the product is worked up to give the desired ester.

h. Saponification of Tetraester

The tetraester of Step g can be saponified in methanol/water, 1:1, and K$_2$CO$_3$. The solution is acidified to pH 7, and dried to give the desired tetraacid ligand. This material is useful as a ligand in this invention.

i. 2,6-bis[N,N-di(carboxymethyl)amino-methyl]4-(4-nitrophenyl)-pyridine tetramethyl ester Fuming nitric acid (0.03 ml, 0.4325 mmol) is added at room temperature to a solution of trifluoromethanesulfonic acid in methylene chloride (4 ml). After stirring for 5 minutes, a solution of 2,6-bis-[N,N-di(carboxymethyl)aminomethyl]-4-phenyl-pyridine tetramethyl ester from step g (860 mg, 0.173 mmol) in a small amount of methylene chloride is slowly added at 0° C. The solution is allowed to warm to room temperature and stirring is continued for one hour. The reaction mixture is then poured onto ice and the mixture is neutralized with sodium carbonate. Extraction with methylene chloride followed by drying over sodium sulfate and evaporation gives 90 mg of crude product.

j. 2,6-bis[N,N-di(carboxymethyl)-aminomethyl]-4-(4-aminophenyl)-pyridine tetramethyl ester (17, below)

The crude product from the above reaction (90 mg, 0.17 mmol) is dissolved in ethanol (13 ml). 10 mg of 10% Pd/C is added and the mixture is stirred at room temperature under one atmosphere of hydrogen for one hour. The catalyst is removed by filtration and the solvent evaporated to give 60 mg of the 4-amino compound. The 3-amino compound (51 mg) is prepared similarly from 70 mg (0.129 mmol) of the corresponding 3-nitro compound. If desired, these or similar aryl pyridines having amine substituents on their aryl rings can be reacted with thiophosgene to convert the amine to an isothiocyanate which in turn can couple to amine-containing antibody-like molecules or the like.

(1) With the above tetraester starting material in hand, this preparation can be carried out following Reaction Sequence 6. In the first reaction, 5.16 μl (1 μmol) of a chloroform solution of 4-amino-tetraester 17 (of j.) is placed in a reaction vial. Solvent is evaporated under argon. One ml of methanol is added followed by 4 μl of 1 N NaOH in methanol. The reaction mixture is stirred overnight at room temperature. Then 50 μl of 20 mM SPDP in ethanol (1 μmol) is added with stirring. The reaction proceeds for one hour to yield 18. One μmol of DTT in ethanol is added and stirred for one hour after which solvent is evaporated to yield ligand 19. Ten μmols of affinity chromatography-purified anti-theophylline antibody, identified as lot number "CA #007" is diluted to 750 μl with 10 mM phosphate buffered saline (PBS). Then 116 μg (0.37 μ mols) of SPDP is added and reacted with stirring at room temperature for 45 minutes to yield leashed antibody 20 which is recovered by ultrafiltration. 400 μmols of ligand 19 are then mixed with antibody 20 in methanol and water in a molar ratio of ligand to antibody of about 40:1 and stirred overnight at room temperature to obtain ligand-labeled antibody 21. Based on the projections in PROC. NATL. ACAD. SCI., 77, 4539, (1980), one might expect there to be about four ligand attachment sites per antibody, on average. The reaction product is filtered and ultrafiltered against PBS to remove all unreacted ligand.

Reaction Sequence 6

-continued

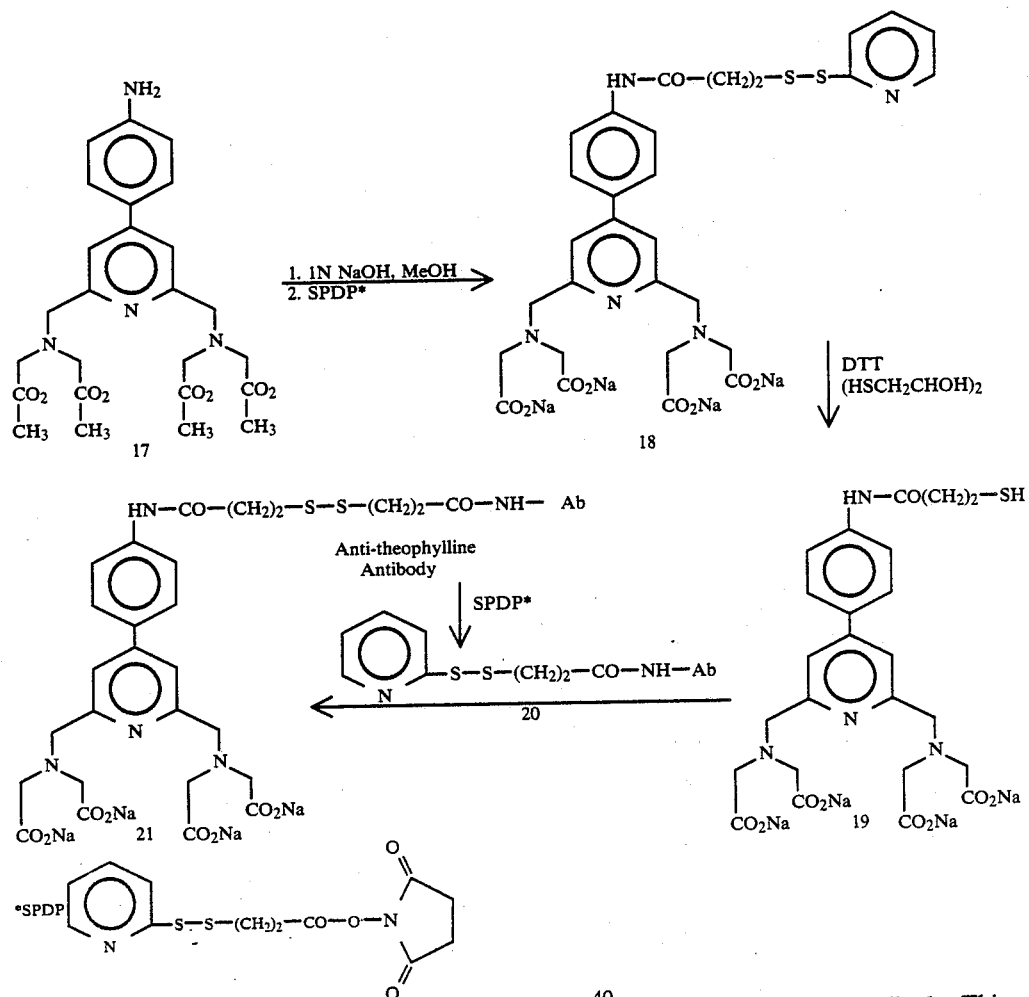

(2) This preparation follows Reaction Sequence 7. It begins with ligand 22 which is prepared from the 3-amino-tetraester of Part j above. One µmol of 22 in 57.4 µl of water is added to 36.8 µl (1 µmol) of DSS (Pierce Chemical) in DMSO. After 5 minutes at room temperature, 100 nmols of the resulting cloudy suspension of 23 is added to 10 nmols of affinity chromatography-purified anti-theophylline antibody. This mixture is held at room temperature for 15 minutes and then quenched with an equal volume (38.6 µl) of 1M ammonium acetate to yield leashed antibody 24 which is recovered by ultrafiltration. This antibody coupling is then repeated using the remaining 900 nmols of 23 and 9 nmols of antibody (ligand: antibody ratio of 100:1).

Reaction Sequence 7

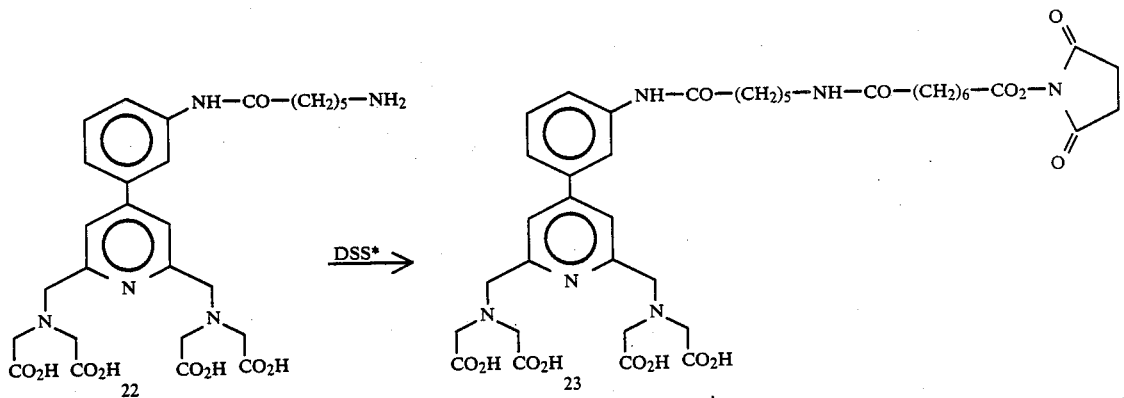

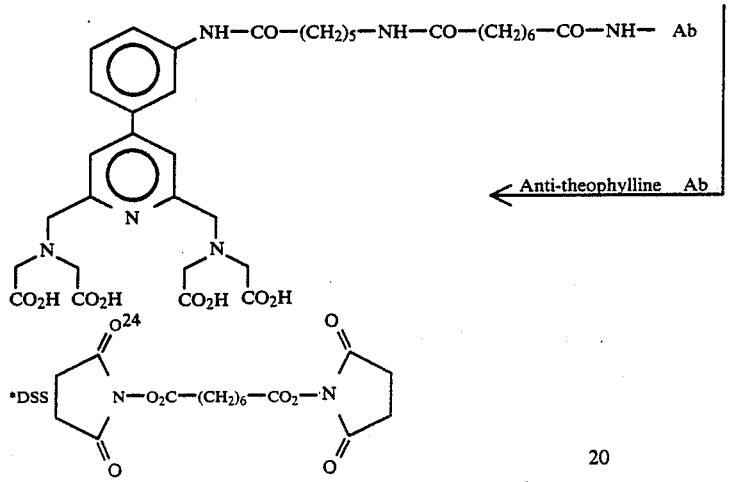

(3) This preparation follows Reaction Sequence 8. It is substantially a repeat of the last preparation with the molar ratio of ligand to antibody is employed to yield labeled anti-theophylline antibody 26.

Reaction Sequence 8

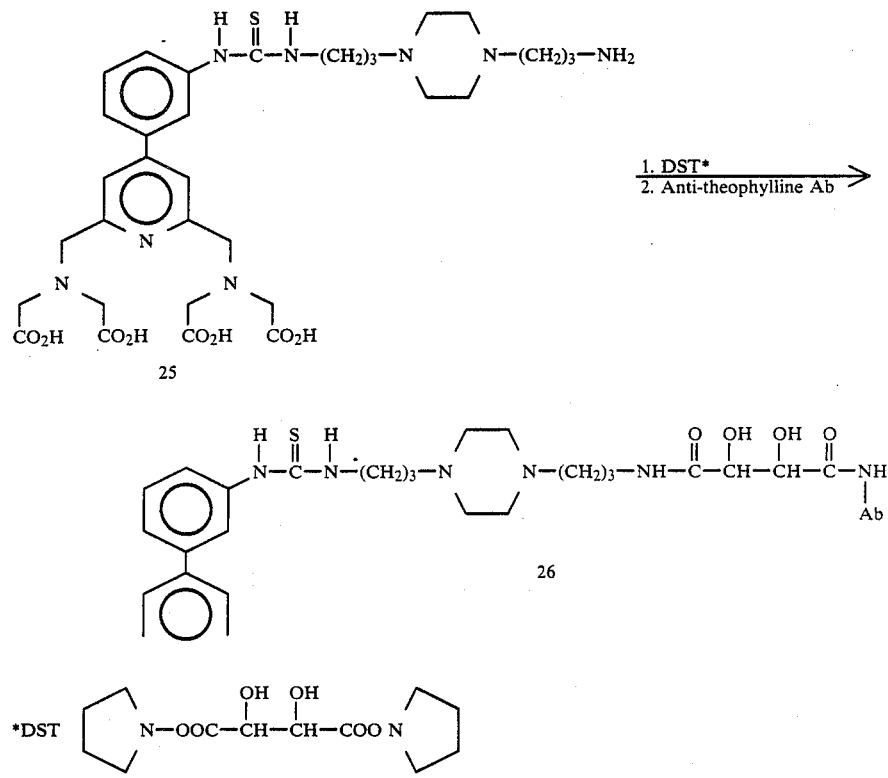

change that it begins with ligand 25 which is prepared from the 3-amino-tetraester of Part j above and that it uses Pierce Chemical DST as coupling agent. A 100:1

(4) As shown in Reaction Sequence 9, this preparation is a repeat of preparation (3) above using Pierce Chemical DSS as coupling agent to yield labeled anti-theophylline antibody 27.

Reaction Sequence 9

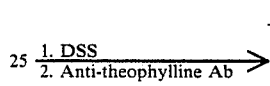

Reaction Sequence 9

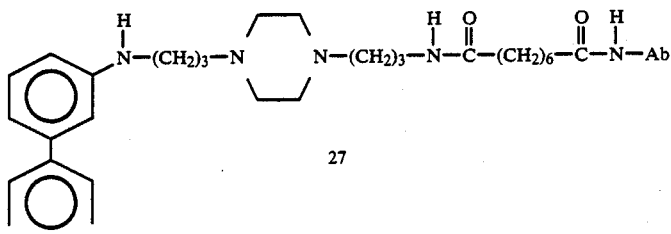

These preparations illustrate that ligands can be attached to antibodies through a wide range of lengths of linking groups so as to achieve proper control of ligand to ligand distances and facilitate metal transfer between such ligands.

D. Conducting the Assay

Terbium chelates of the theophylline-linked tri- and tetraacids prepared above are prepared as follows. The tri- and tetraacids of these preparations are separately dissolved in 0.01M sodium borate solution to a concentration of $10^{-5}$M. Then an equivalent molar amount of aqueous terbium chloride is added to each and the mixtures are allowed to stand for a few minutes. Fluorescence measurements are carried out and demonstrate that 1:1 molar chelate complexes of the tetraacids and the terbium have been formed and that such complexes are stable but only modestly fluorescent.

An assay for theophylline is carried out by allowing one of the terbium chelate-labeled theophyllines to compete with theophylline standards for binding to one of the second ligand-linked anti-theophylline antibodies of preparations (1) through (4) of C. above. The labeled theophylline on binding to antibody brings its terbium ion into close proximity of the second ligand attached to the antibody. The terbium ion is directly transferred to this second ligand thus forming a new chelate complex with the second ligand which is highly fluorescent and easily detectable using fluorescence-background rejection methods. The formation of this new chelate brings about an enhancement of its fluorescence and this enhancement is proportional to the amount of labeled theophylline bound and inversely proportional to the amount of theophylline present in the sample. The assay is carried out in polystyrene tubes (12×15 mm) to which 1 ml of pH 8.5 0.01M sodium borate buffer was added. This is followed by the addition of 10 μl of 1 μM tracer (8.7 ng) and 10 μl of theophylline standard (0, 5.4, 16.2, 54, and 540 ng). Addition of 25 μl of an about 0.3 μM solution of the second chelate-labeled anti-theophylline antibody in 0.01M borate containing 0.1M sodium chloride and 1% normal human serum (final concentration in assay tube about 7.5 nM) leads to increases in the observed fluorescence which are inversely proportional to the levels of theophylline in the samples.

What is claimed is:

1. In a method of chemical analysis for determining an analyte in a test material comprising carrying out a biospecific reaction with the analyte and thereafter detecting the occurrence of the biospecific reaction and employing a reporter mechanism to indicate the occurrence of the biospecific reaction the improvement comprising employing as the reporter mechanism an interligand metal ion transfer in which a metal ion is directly transferred from a first chelate complex with a first ligand to a second ligand thereby forming a second chelate complex which is separate from and detectably different from the first chelate complex.

2. The method of analysis of claim 1 wherein the analyte is isolated from the test material prior to the interligand metal ion transfer.

3. The method of claim 2 wherein the biospecific reaction is a competitive reaction in which the analyte competes with an added chelate-labeled competitor of the analyte.

4. The method of claim 3 comprising the steps of
   a. biospecifically reacting in the presence of the test material two species capable of biospecific reaction with one another, the second of which carries a first metal ion chelate complex and competes with the analyte, if present, for a reaction-limiting amount of one or more biospecific binding sites on the first species thereby forming a biospecific reaction product,
   b. separating the biospecific reaction product from unreacted second species and analyte,
   c. contacting the separated biospecific reaction product with an excess of a ligand which directly removes metal ion from the first metal ion chelate and forms a second metal ion chelate which is separate from and detectably different from the first metal ion chelate,
   d. detecting the presence of the second metal ion chelate complex and generating a signal related thereto, and
   e. quantitatively comparing the generated signal with signals from known standards to determine the amount of the analyte in the test material.

5. The method of claim 4 wherein the first species is attached to a solid support.

6. The method of claim 3 comprising the steps of
   a. biospecifically reacting in the presence of the test material first and second biospecific species, said first species carrying a first metal ion chelate complex and capable of biospecific reaction with the analyte and said second species being capable of reaction with said first species in competition with said analyte if present, for a reaction-limiting amount of biospecific binding sites on the first species thereby forming a biospecific reaction product,
   b. separating the biospecific reaction product from unreacted second species and analyte,
   c. contacting the separated biospecific reaction product with an excess of a ligand which directly removes metal ion from the first metal ion chelate complex and forms a second metal ion chelate complex which is separate from and detectably different from the first metal ion chelate complex, d. detecting the presence of the second metal ion chelate complex and generating a signal related thereto, and e. quantitatively comparing the generated signal with signals from known standards to determine the amount of the analyte in the test material.

7. The method of claim 6 wherein the second species is attached to a solid support.

8. The method of claim 2 comprising the steps of
   a. contacting the test material with an excess of a biospecific partner for a first site on the analyte, thereby biospecifically coupling any analyte present in the test sample to form a first biospecific pair,
   b. contacting the first biospecific pair with an excess of a second biospecific partner for a second site on the analyte, which second biospecific partner carries a first metal ion chelate complex thereby forming a first metal ion chelate-labeled biospecific trio,
   c. separating the biospecific trio from unreacted second biospecific partner,
   d. contacting the separated biospecific trio with an excess of a ligand which directly removes metal ion from the first metal ion chelate complex and forms a second metal ion chelate complex which is separate from and detectably different from the first metal ion chelate and the metal ion-containing biospecific trio,
   e. detecting the presence of the second metal ion chelate complex and generating a signal related thereto, and
   f. quantitatively comparing the generated signal with signals from known standards to determine the amount of the analyte in the test material.

9. The method of analysis of claim 8 wherein the biospecific partner for the first site on the analyte is attached to a solid support.

10. The method of analysis of claim 1 wherein the analyte is not isolated from the test material prior to the interligand metal ion transfer.

11. The method of claim 10 wherein the biospecific reaction is a competitive reaction in which the analyte competes with an added chelate-labeled competitor of the analyte.

12. The method of claim 10 comprising the steps of
   a. biospecifically reacting in the presence of the test material two species capable of biospecific reaction with one another, the first of which carries a first metal ion chelate complex and the second of which carries a second metal ion chelate-forming ligand, said second species competing with the analyte, if present, for a reaction-limiting amount of one or more biospecific binding sites on the first species thereby forming a biospecific reaction product comprising the couple of the first and second species and the couple of the first species and the analyte, the ligand on the second species being positioned in such proximity to its biospecific group that as a result of the biospecific reaction the ligand can contact and react with the first metal ion chelate complex carried by the first species,
   b. incubating the product of the biospecific reaction for a period sufficient to effect direct interligand transfer of metal ion from the first metal ion chelate complex to the second metal ion chelate-forming ligand thereby forming a second metal ion chelate complex,
   c. detecting the presence of the second metal ion chelate complex and generating a signal related thereto, and
   d. quantitatively comparing the generated signal with signals from known standards to determine the amount of the analyte in the test material.

13. The method of claim 11 comprising the steps of
   a. biospecifically reacting in the presence of the test material two species capable of biospecific reaction with one another, the second of which carries a first metal ion chelate complex and the first of which carries a second metal ion chelate-forming ligand, said second species competing with the analyte, if present, for a reaction-limiting amount of one or more biospecific binding sites on the first species thereby forming a biospecific reaction product comprising the couple of the first and second species and the couple of the first species and the analyte, the ligand on the first species being positioned in such proximity to its biospecific group that as a result of the biospecific reaction the ligand can contact and react with the first metal ion chelate complex carried by the second species,
   b. incubating the product of the biospecific reaction for a period sufficient to effect direct interligand transfer of metal ion from the first metal ion chelate complex to the second metal ion chelate-forming ligand thereby forming a second metal ion chelate complex,
   c. detecting the presence of the second metal ion chelate complex and generating a signal related thereto, and
   d. quantitatively comparing the generated signal with signals from known standards to determine the amount of the analyte in the test material.

14. The method of claim 10 comprising the steps of
   a. biospecifically reacting in the presence of the test material two biospecific species, one of which carries a first metal ion chelate complex and the other of which carries a second metal ion chelate-forming ligand, each of these biospecific species being present in excess and each biospecifically reacting with the analyte if present but with different sites thereon, the chelate on the first species and the ligand on the second species each being positioned in such proximity that as a result of the biospecific reactions the ligand can contact and react with the first metal ion chelate complex,
   b. incubating the product of the biospecific reaction for a period sufficient to effect direct interligand transfer of metal ion from the first metal ion chelate complex to the second metal ion chelate-forming ligand thereby forming a second metal ion chelate complex,
   c. detecting the presence of the second metal ion chelate complex and generating a signal related thereto, and
   d. quantitatively comparing the generated signal with signals from known standards to determine the amount of the analyte in the test material.

15. The method of claim 1 wherein the first chelate complex is fluorescent and the detectable difference between the first and second chelate complexes is a difference in fluorescence.

16. The method of claim 15 wherein the fluorescence is measured using a fluorescent background rejection method in which the difference in fluorescence is measured after background fluorescence has decayed.

17. The method of claim 1 wherein the second chelate complex is fluorescent and the detectable difference between the first and second chelate complexes is a difference in fluorescence.

* * * * *